(12) United States Patent
Birkle et al.

(10) Patent No.: US 12,421,844 B2
(45) Date of Patent: Sep. 23, 2025

(54) METHOD TO ASSESS RESERVOIR CONTINUITY BETWEEN SINGLE WELLS IN AN OILFIELD FORMATION WITHIN A REGION WITH SEVERAL PETROLEUM RESERVOIRS

(71) Applicant: SAUDI ARABIAN OIL COMPANY, Dhahran (SA)

(72) Inventors: Peter Birkle, Dhahran (SA); Maram Saif, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 470 days.

(21) Appl. No.: 17/936,728

(22) Filed: Sep. 29, 2022

(65) Prior Publication Data

US 2024/0117730 A1 Apr. 11, 2024

(51) Int. Cl.
*E21B 47/10* (2012.01)
*E21B 49/08* (2006.01)
*G01N 33/18* (2006.01)

(52) U.S. Cl.
CPC .......... *E21B 47/10* (2013.01); *E21B 49/0875* (2020.05); *G01N 33/18* (2013.01)

(58) Field of Classification Search
None
See application file for complete search history.

(56) References Cited

U.S. PATENT DOCUMENTS

| | | | |
|---|---|---|---|
| 4,269,271 A * | 5/1981 | Shupe | C09K 8/584 166/270.1 |
| 7,584,086 B2 | 9/2009 | Frankel | |
| 8,437,997 B2 | 5/2013 | Meurer et al. | |
| 8,776,895 B2 | 7/2014 | Li et al. | |
| 9,316,761 B2 | 4/2016 | Edwards et al. | |
| 9,416,656 B2 | 8/2016 | Pomerantz et al. | |
| 10,620,107 B2 | 4/2020 | Weiss et al. | |
| 10,746,017 B2 | 8/2020 | Zuo et al. | |

(Continued)

FOREIGN PATENT DOCUMENTS

RU 2754741 C1 9/2021

OTHER PUBLICATIONS

James, Gareth et al, "An Introduction to Statistical Learning: with Applications in R," Springer Science & Business Media, published 2013, pp. 26-28, 375-377, 385-386, 398 (Year: 2013).*

(Continued)

*Primary Examiner* — Andrew Schechter
*Assistant Examiner* — Ethan Wesley Edwards
(74) *Attorney, Agent, or Firm* — Osha Bergman Watanabe & Burton LLP

(57) ABSTRACT

A method to assess reservoir continuity between single wells in an oilfield formation within a region with several petroleum reservoirs, including the steps: collecting water samples from each of the single wells, obtaining the geochemical composition of each of the water samples, obtaining a dataset from the geochemical compositions of the single wells, analyzing the dataset using principal component analysis to obtain principal components of the dataset, clustering the principal components to obtain clusters, identifying hydrodynamic groups from the clusters, assigning the wells to hydrodynamic groups, wherein wells within one single hydrodynamic group are considered to be hydraulically communicated.

10 Claims, 13 Drawing Sheets

(56) References Cited

U.S. PATENT DOCUMENTS

| | | | |
|---|---|---|---|
| 11,021,948 B2 | 6/2021 | Aslanian et al. | |
| 2010/0204511 A1* | 8/2010 | Horton | E21B 21/068 562/512 |
| 2019/0316166 A1* | 10/2019 | Summers | E21B 43/16 |

OTHER PUBLICATIONS

"Geochemistry and depositional environment of the Mesoproterozoic Xiamaling shales, northern North China", Jin Wu et al., Journal of Petroleum Science and Engineering, vol. 215, Part B, Aug. 2022 (Year: 2022).*

R. Al-Obaid et al.; "Inter-reservoir Communication Detection via Pressure Transient Analysis: Integrated Approach", SPE-87039; Society of Petroleum Engineers; Mar. 2004; pp. 1-6 (6 pages).

L. Belkhiri et al.; "Statistical categorization geochemical modeling of groundwater in Ain Azel plain (Algeria)", Journal of African Earth Sciences; vol. 59; Oct. 29, 2010; pp. 140-148 (9 pages).

B. K. Chaudhary et al.; "Spatial variability of produced-water quality and alternative-source water analysis applied to the Permian Basin, USA", Hydrogeology Journal; vol. 27; Nov. 19, 2019; pp. 1-17 (17 pages).

V. Cloutier et al.; "Multivariate statistical analysis of geochemical data as indicative of the hydrogeochemical evolution of groundwater in a sedimentary rock aquifer system", Journal of Hydrology; vol. 353; Issues 3-4; May 30, 2008; pp. 294-313 (20 pages).

M. A. Engle et al.; "Geochemistry of formation waters from the Wolfcamp and 'Cline' shales: Insights into brine origin, reservoir connectivity, and fluid flow in the Permian Basin, USA", Chemical Geology; vol. 425; Jan. 30, 2016; pp. 76-92 (17 pages).

I. M. Farnham et al.; "Deciphering Groundwater Flow Systems in Oasis Valley, Nevada, Using Trace Element Chemistry, Multivariate Statistics, and Geographical Information System", Mathematical Geology; vol. 32; No. 8; 2000; pp. 943-968 (26 pages).

K. Ghorayeb and A. Firoozabadi; "Molecular, Pressure, and Thermal Diffusion in Nonideal Multicomponent Mixtures", Fluid Mechanics and Transport Phenomena; AIChE Journal; vol. 46; Issue 5; May 2000; pp. 883-891 (9 pages).

C. Güler et al.; "Evaluation of graphical and multivariate statistical methods for classification of water chemistry data", Hydrogeology Journal; vol. 10; May 9, 2002; pp. 455-474 (20 pages).

H. Iwamori et al.; "Classification of geochemical data based on multivariate statistical analyses: Complementary roles of cluster, principal component, and independent component analyses", Geochemistry, Geophyics, Geosystems; AGU Publications; vol. 18; Issue 3; Mar. 17, 2017; pp. 994-1012 (19 pages).

H. F. Kaiser; "The Varimax Criterion For Analytic Roation in Factor Analysis", Psychometrika; vol. 23; No. 3; Sep. 1958; pp. 187-200 (14 pages).

C. Liu et al.; "Application of factor analysis in the assessment of groundwater quality in a blackfoot disease area in Taiwan", The Science of the Total Enviroment; vol. 313; Issues 1-3; Sep. 1, 2003; pp. 77-89 (13 pages).

F. Liu et al.; "Geochemical characterization of shallow groundwater using multivariate statistical analysis and geochemical modeling in an irrigated region along the upper Yellow River, Northwestern China", Journal of Geochemical Exploration; vol. 215; May 11, 2020; pp. 1-13 (13 pages).

J. L. Mari and F. Delay; "Contribution of Seismic and Acoustic Methods to Reservoir Model Building", in Hydraulic Conductivity—Issues, Determination and Applications; IntechOpen; Ch. 17; Nov. 23, 2011; pp. 329-354 (26 pages).

A. Mukanov and A. Aldazhar; "The Role of Pressure Observation and Pressure Transient Analysis in Changing the Geological Concept of Mature Oil Field", SPE-198333-MS; Society of Petroleum Engineers; Oct. 2019; pp. 1-6 (6 pages).

C. U. Ohaeri et al.; "Evaluation of Reservoir Connectivity and Hydrocarbon Resource Size in a Deep Water Gas Field Using Multi-Well Interference Tests", SPE-170829-MS; Society of Petroleum Engineers; Oct. 2014; pp. 1-13 (13 pages).

K.E. Peters et al.; "Geochemical Screening", in: The Biomarker Guide vol. 1; Ch. 4; Jan. 2010; pp. 72-118 (46 pages).

L. Ribeiro and M. E. Macedo; "Application of multivariate statistics, trend- and cluster analysis to groundwater quality in the Tejo and Sado Aquifer", Groundwater Quality: Remediation and Protections (Proceedings of the Prague Conference); No. 225; May 1995; pp. 39-47 (9 pages).

P.P. Schot and J. van der Wal; "Human impact on regional groundwater composition through intervention in natural low patterns and changes in land use", Journal of Hydrology; vol. 134; Issues 1-4; Jun. 1992; pp. 297-313 (17 pages).

J. L. Shelton et al.; "Machine Learning Can Assign Geologic Basin to Produced Water Samples Using Major Ion Geochemistry", Natural Resources Research; vol. 30; No. 6; Dec. 2021; pp. 4147-4163 (17 pages).

P. C. Smalley et al.; "Spatial 87Sr/86Sr variations in formation water and calcite from the Ekofisk chalk oil field: Implications for reservoir connectivity and fluid composition", Applied Geochemistry; vol. 7; Issue 4; Jul. 1992; pp. 341-350 (10 pages).

R. K. Steinhorst and R. E. Williams; "Discrimination of Groundwater Sources Using Cluster Analysis, MANOVA, Canonical Analysis and Discriminant Analysis", Water Resources Research; vol. 21; No. 8; Aug. 1985; pp. 1149-1156 (8 pages).

P. Vrolijk et al.; "Reservoir Connectivity Analysis—Defining Reservoir Connections and Plumbing", SPE-93577-PP; Society of Petroleum Engineers; Mar. 2005; pp. 1-23 (23 pages).

H. Tian et al.; "New insights into the volume and pressure changes during the thermal cracking of oil to gas in reservoirs: Implications for the in-situ accumulation of gas cracked form oils", AAPG Bulletin; vol. 92; No. 2; Feb. 2008; pp. 181-200 (20 pages).

* cited by examiner

METHOD TO ASSESS RESERVOIR CONTINUITY BETWEEN SINGLE WELLS IN AN OILFIELD FORMATION WITHIN A REGION WITH SEVERAL PETROLEUM RESERVOIRS

BACKGROUND

Darcy's law describes the flow of a fluid through a porous medium, which states that the flow rate is proportional to the pressure change between the inlet and outlet of the porous medium. Similarly, the dynamic behavior of non-solid phases, such as oil, gas, or water, in petroleum systems is defined by Darcy's law.

Knowledge of the production time-scale reservoir connectivity for a specific subsurface region is essential for the management of exploration and production assets in oil and gas fields. The quantitative assessment of dynamic connectivity features between single wells, structural blocks, and single reservoirs on a small, intermediate, and large scale, respectively, is a prerequisite to define the shape and volume of the prospected reservoir. The determination of connection between different compartments in a reservoir is highly helpful for well performance evaluation, field re-development and in-fill drilling programs.

The Reservoir Connectivity Analysis (RCA) is a refined series of analyses and approaches to integrate structural, stratigraphic analysis of sedimentary rock layers, and fluid pressure and composition data into a permissible set of scenarios of fluid contacts and pressures. RCA has three basic components:

1) A geological compartment description of the lithological units based on cuttings and core material with structural details on the presence of fault and fracture by geophysical methods, e.g., 3D-seismic;
2) Connection between compartments are traced by subsurface fluid pressure gradients, which are based on reservoir temperature, pressure, and fluid composition and pressure-volume-temperature (PVT) properties. As a basic assumption, fluid pressure data on either side of a compartment connection window must lie on the same fluid pressure line for each fluid type in contact across that window; and
3) An RCA model built to integrate reservoir geometry with interpreted connections and arrows for interpreted system exit leaks. The RCA model may be used for various development and production strategies, e.g., determining well placement and/or predicting hydrocarbon production based on one or several production scenarios.

RCA requires an extended dataset from cutting and core material, 3-D seismic imaging, PVT tests, and modeling software. Therefore, RCA is slow, less economic, and less straightforward. Accordingly, there exists a need for a method to assess reservoir continuity between single wells in an oilfield formation within a region with several petroleum reservoirs.

SUMMARY

This summary is provided to introduce a selection of concepts that are further described below in the detailed description. This summary is not intended to identify key or essential features of the claimed subject matter, nor is it intended to be used as an aid in limiting the scope of the claimed subject matter.

In one aspect, embodiments disclosed herein relate to a method to assess reservoir continuity between single wells in an oilfield formation within a region with several petroleum reservoirs, comprising the steps: collecting water samples from each of the single wells, obtaining the geochemical composition of each of the water samples, obtaining a dataset from the geochemical compositions of the single wells, analyzing the dataset using principal component analysis to obtain principal components of the dataset, clustering the principal components to obtain clusters, identifying hydrodynamic groups from the clusters, assigning the wells to hydrodynamic groups, wherein wells within one single hydrodynamic group are considered to be hydraulically communicated.

Other aspects and advantages of the claimed subject matter will be apparent from the following description and the appended claims.

BRIEF DESCRIPTION OF DRAWINGS

Specific embodiments of the disclosed technology will now be described in detail with reference to the accompanying figures. Like elements in the various figures are denoted by like reference numerals for consistency.

DETAILED DESCRIPTION

Figure 1:
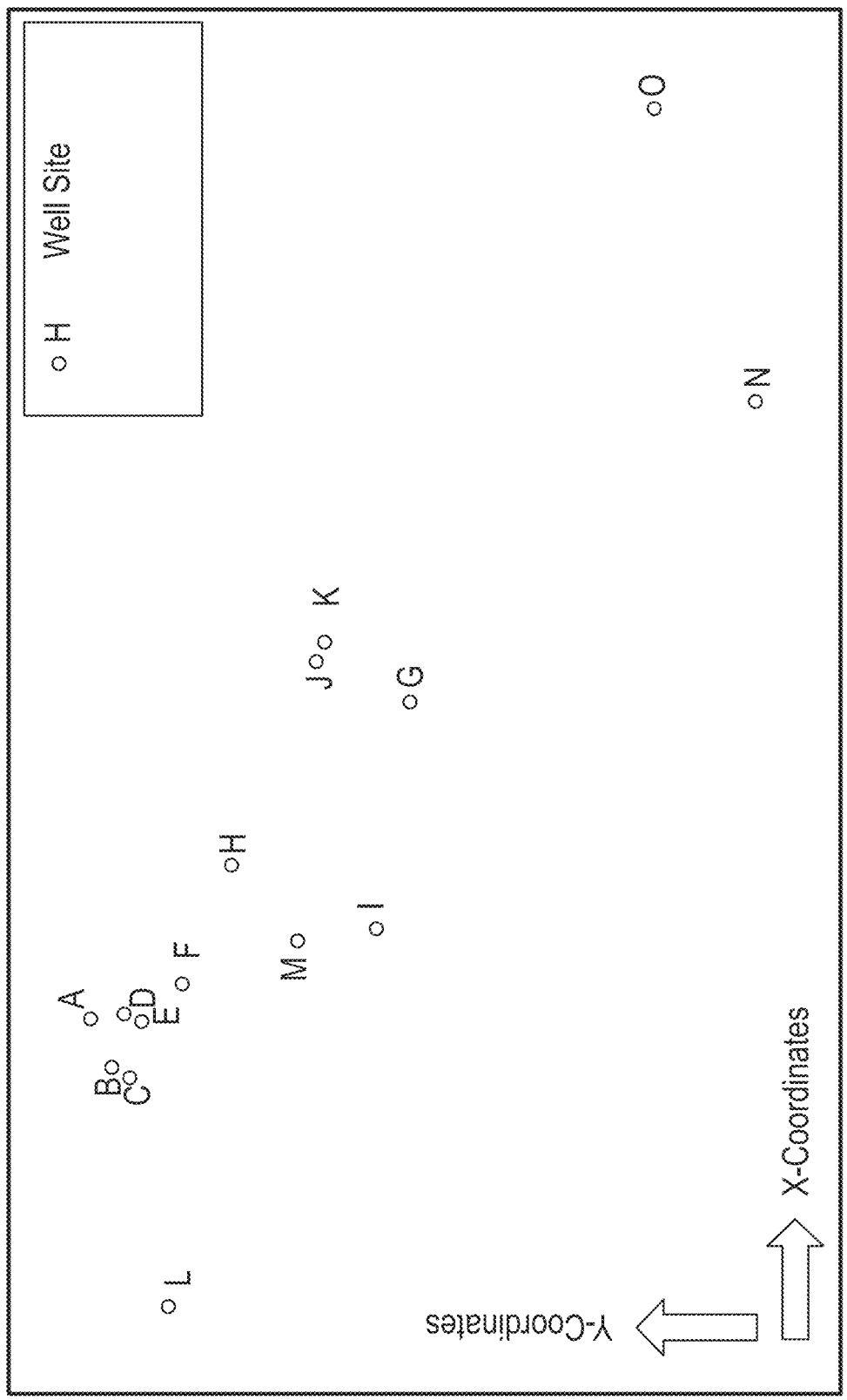
FIG. 1 shows an oilfield environment having single wells within a region with several petroleum reservoirs, according to one or more embodiments.

In the following detailed description of embodiments of the disclosure, numerous specific details are set forth in order to provide a more thorough understanding of the disclosure. However, it will be apparent to one of ordinary skill in the art that the disclosure may be practiced without these specific details. In other instances, well-known features have not been described in detail to avoid unnecessarily complicating the description.

Throughout the application, ordinal numbers (e.g., first, second, third, etc.) may be used as an adjective for an element (i.e., any noun in the application). The use of ordinal numbers is not to imply or create any particular ordering of the elements nor to limit any element to being only a single element unless expressly disclosed, such as using the terms "before", "after", "single", and other such terminology. Rather, the use of ordinal numbers is to distinguish between the elements. By way of an example, a first element is distinct from a second element, and the first element may encompass more than one element and succeed (or precede) the second element in an ordering of elements.

It is to be understood that the singular forms "a," "an," and "the" include plural referents unless the context clearly dictates otherwise. Thus, for example, reference to "a marine source fluid sample" includes reference to one or more of such samples.

Terms such as "approximately," "substantially," etc., mean that the recited characteristic, parameter, or value need not be achieved exactly, but that deviations or variations, including for example, tolerances, measurement error, measurement accuracy limitations and other factors known to those of skill in the art, may occur in amounts that do not preclude the effect the characteristic was intended to provide.

It is to be understood that one or more of the steps shown in the flowchart may be omitted, repeated, and/or performed in a different order than the order shown. Accordingly, the scope disclosed herein should not be considered limited to the specific arrangement of steps shown in the flowchart.

Although multiple dependent claims are not introduced, it would be apparent to one of ordinary skill that the subject matter of the dependent claims of one or more embodiments may be combined with other dependent claims.

Embodiments disclosed herein relate to a method to assess reservoir continuity between single wells in an oilfield formation within a region with several petroleum reservoirs. Specifically, embodiments disclosed herein utilize a combination of geochemical data from oilfield water with statistical methods to trace reservoir connectivity in petroleum systems. The core of embodiments disclosed herein lies in the utilization of statistical methods on inorganic geochemical data from representative formation water samples to assess the potential of reservoir connectivity between well bores or regional field structures.

The basic assumption for the methodology disclosed herein is that the migration of gas and liquid (oil, water) phases has an analogue flow behavior in petroleum systems. Secondly, groundwater or formation water from different geological terrains show contrasting geochemical fingerprints, while communicated groundwater systems are characterized by gradual trend for their compositional alteration. The migration behavior of formation water can therefore be utilized as an indirect tool to track flow patterns of hydrocarbons. For the scenario of a dynamic flow behavior without barriers, primary pore water from two connected pay zones become homogenized in their geochemical composition by the mixing of both fluid types. In the contrasting case with the presence of isolated reservoir sections, groundwater systems on both sides of the hydraulic barrier undergo different evolution processes with a resulting differentiation in their geochemical composition.

The method to assess reservoir continuity provides a combination of geochemical data from oilfield water with statistical methods to trace reservoir connectivity in petroleum systems. The assessment of reservoir connectivity is approached by numerical (flow modeling), physical (gravity, fluorescence, acoustic noise), logging tools (MDT, DST), geochemical (organics, isotopes) methods. The utilization of statistical methods on inorganic geochemical data from representative formation water samples assesses the potential of reservoir connectivity between well bores or regional field structures.

A basic assumption for the methodology is that the migration of gas and liquid (oil, water) phases has an analogue flow behavior in petroleum systems. Secondly, groundwater or formation water from different geological terrains show contrasting geochemical fingerprints, while communicated groundwater systems are characterized by gradual trend for their compositional alteration. The migration behavior of formation water can therefore be utilized as an indirect tool to track flow patterns of hydrocarbons. For the scenario of a dynamic flow behavior without barriers, primary pore water from two connected pay zones become homogenized in their geochemical composition by the mixing of both fluid types. In the contrasting case with the presence of isolated reservoir sections, groundwater systems on both sides of the hydraulic barrier undergo different evolution processes with a resulting differentiation in their geochemical composition.

FIG. 1 shows single wells A-O in an oilfield formation within a region with several petroleum reservoirs. The method disclosed herein assesses reservoir continuity between two or three of the single wells A-O. In one or more embodiments, the petroleum reservoirs are oil or gas reservoirs.

The reservoirs may be clastic or carbonate reservoirs. The clastic reservoirs include clastic rocks composed of fragments (clasts) of minerals and rocks. The clast includes a fragment of geological particles of rock, chunks and smaller grains of rock broken off.

The carbonate reservoir includes carbonate rocks (class of sedimentary rocks) that include carbonate minerals. In some embodiments, the carbonate rocks include limestone, which includes calcite or aragonite, or dolomite rocks, which include mineral dolomite.

The petroleum reservoirs may be unconventional or conventional reservoirs. The main difference is that unconventional reservoirs do not have traps and in conventional reservoirs buoyancy is the driving force for the petroleum accumulation. In unconventional reservoirs the oil is contained within the source rock. Therefore, unconventional reservoirs require mining rather than drilling and pumping as in a conventional reservoir. Mining has higher postproduction costs making unconventional reservoirs less profitable compared to conventional reservoirs.

Traps form when the hydrocarbons migrating upward are stopped by sealing. Traps have three categories: structural traps, stratigraphic traps, and hydrodynamic traps. Structural traps are formed when the structure of the reservoir changes due to folding and faulting. Structure change in the reservoir creates domes, anticlines, and folds. Stratigraphic traps form when thickness, texture, porosity, or lithology of the reservoir rock undergoes lateral and vertical variations. Stratigraphic traps include unconformity traps, lens traps, and reef traps. Hydrodynamic traps are less common and are caused by the differences in water pressure of flowing water, creating a tilt at the contact between the hydrocarbon and the water. Traps include a seal (cap rock) that prevents hydrocarbons from further upward migration.

Figure 2:
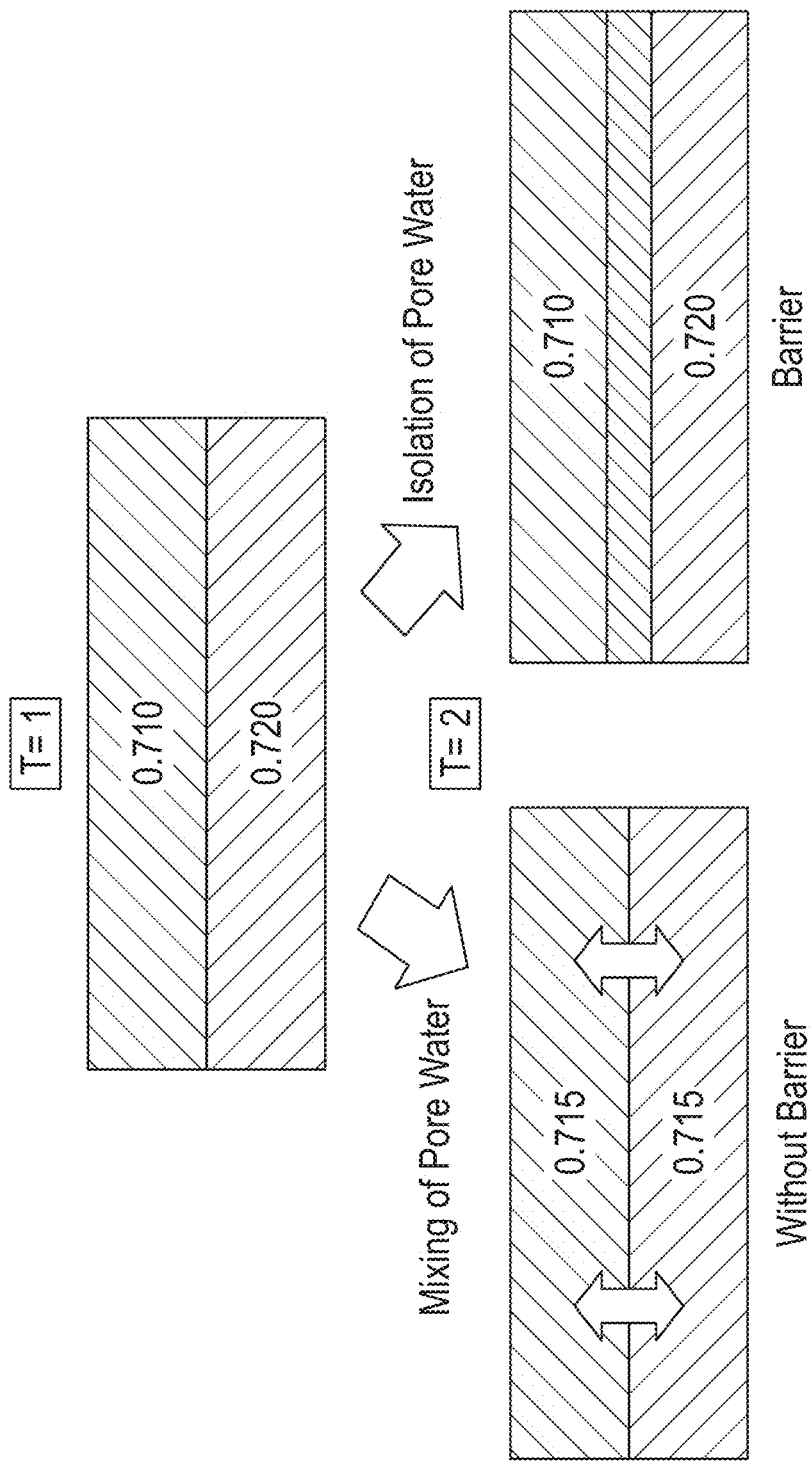
FIG. 2 shows the geochemical fingerprints of communicated and compartmentalized reservoirs.

FIG. 2 shows the isotopic fingerprint of two reservoirs with a primary constellation of two reservoirs with different isotopic compositions (T=1) with isotopic fingerprints of 0.710 and 0.720 (upper case). Geochemical fingerprinting is used for data of formation water to interpret hydrocarbon fluids and petrophysical well logs for the assessment of lateral and vertical migration pathways. The isotopic fingerprint is the ratio of stable non-radiogenic isotopes, stable radiogenic isotopes, or unstable radioactive isotopes in a material. The ratios of the isotopes in a material are measured by isotope analysis. Formation waters from different geological terrains or origins will show contrasting isotope fingerprints.

Two scenarios (T=2) can be distinguished to assess the hydrodynamic properties of reservoirs. Scenario 1: In case that reservoirs are connected, the missing of stratigraphic or structural barriers causes the mixing and isotopic homogenization of primary pore water from two pay zones (lower left case in FIG. 2). Scenario 2: In case that reservoirs are compartmentalized, the presence of sealing units causes the preservation of the primary isotopic composition of both formation water units (lower right case in FIG. 2).

Figure 3:
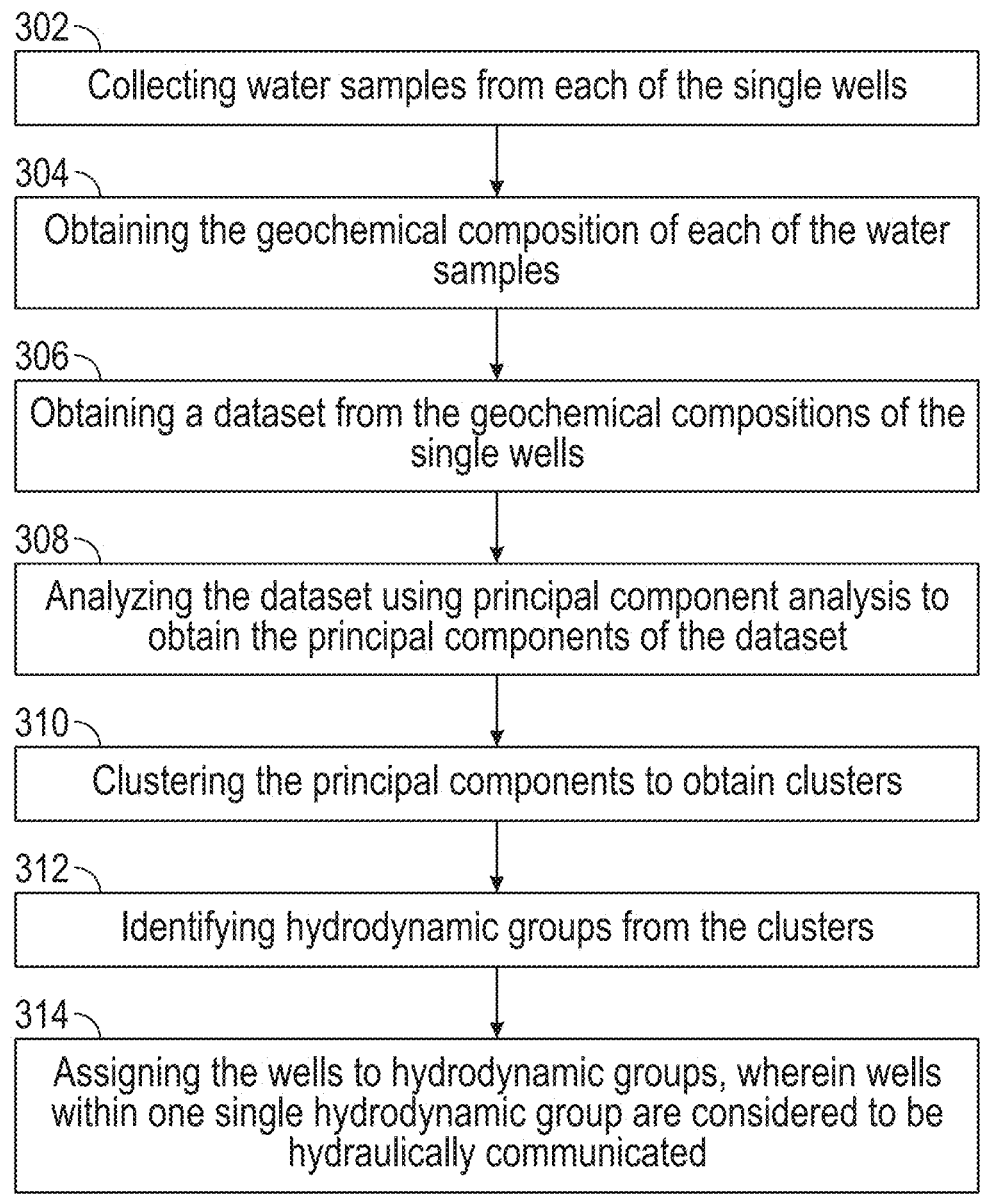
FIG. 3 shows a flowchart of the method steps to assess reservoir continuity between single wells in an oilfield formation within a region with several petroleum reservoirs, according to one or more embodiments.

FIG. 3 shows a flowchart of the method steps to assess reservoir continuity between single wells in an oilfield formation within a region with several petroleum reservoirs.

Initially, in step 302, water samples are collected from each of the single wells, e.g., wells A to O. Oil and gas from underground reservoirs are usually accompanied by water or brine, which is called produced water. The produced water comes from one specific formation, e. g., formation X. In one or more embodiments, 185 water samples are collected from the wells. In other embodiments, 92 water samples are collected. The produced water samples are collected either with bottom hole tools or from surface well installations.

In step 304, the geochemical composition of the water samples is obtained.

In one or more embodiments, the geochemical composition includes concentrations and physical parameters, such as pH, and density, water hydrochemistry, such as total dissolved salinity (TDS), Na, Ca, Mg, K, Cl, HCO3, CO3, SO4, Ba, Sr, and isotopic ratios, such as $\delta^2H$, $\delta^{11}B$, $\delta^{18}O$, $\delta^{18}O_{SO4}$, $\delta^{34}S_{SO4}$, $\delta^{13}C$, $^{14}C$, $\delta^{37}Cl$, $\delta^{87}Sr/^{86}Sr$, $^{36}Cl$, $^{81}Br$, $^{129}I$.

In step 306, a hydro-chemical dataset is obtained from the geochemical compositions of the single wells.

Table 1 shows the dataset of the geochemical compositions (columns) of 15 wells A-O (rows). There are several geochemical compositions measured for each well A-O. Some wells have several rows. However, only one row is selected for each well.

In one or more embodiments, the selection of wells out of the whole dataset, consist of the concentration of 15 elements ($HCO_3$, Ca, Cl, K, Mg, Na, $SO_4$, Ba, Br, Sr, B, Fe, I, Li, Si), plus Total Dissolved Solids (TDS), Specific Gravity (SG), and pH, chosen from 15 water samples (No. 1, 5, 8-10, 12, 15-20, 25, 28-29) from 15 wells (wells A-O from FIG. 1, for example) (Table 1 and 2). These elements include major ($HCO_3$, Ca, Cl, K, Mg, Na, $SO_4$), minor (Ba, Br, Sr), and trace elements (B, Fe, I, Li, Si), plus stable isotopes ($\delta^{18}O$, $\delta^2H$, $\delta^{13}C$, $\delta^{18}O_{SO4}$, $\delta^{34}S_{SO4}$, $\delta^{37}Cl$, $\delta^{11}B$, $\delta^{81}Br$ in Table 3A and 3B) and radiogenic isotopes ($^{14}C$, $^{36}Cl$, $^{87}Sr/^{86}Sr$, $^{129}I$ in Table 3A and 3C), and several elemental ratios. The selection criteria are described in step 905 of FIG. 9. One sample (sample no. 1, 5, 8-10, 12, 15-20, 25, 28, and 29) was selected from each well (well no. A-O).

TABLE 1

Dataset obtained from geochemical composition of produced water samples from formation X with one selected sample (No. 1, 5, 8-10, 12, 15-20, 25, 28, and 29) for each well (well No. A-O).

| Sample No. | Well No. | TDS [mg/L] | SG [g/cm³] | pH | HCO$_3$ [mg/L] | B [mg/L] | Ba [mg/L] | Br [mg/L] | Ca [mg/L] | Cl [mg/L] |
|---|---|---|---|---|---|---|---|---|---|---|
| 1 | A | 15,583 | 1.0125 | 6.7 | 1,708 | 119 | 9 | 48 | 144 | 8,098 |
| 2 | A | 17,442 | 1.013 | 7.2 | 2,483 | 161 | 8 | 85 | 108 | 9,371 |
| 3 | A | 15,457 | 1.0124 | 7.4 | 2,058 | 138 | 9 | 78 | 131 | 7,420 |
| 4 | A | 38,037 | 1.0486 | 7.5 | 549 | 3 | 8 | 204 | 37 | 36,909 |
| 5 | B | 45,087 | 1.0316 | 6.1 | 544 | 25 | 160 | 99 | 749 | 28,003 |
| 6 | B | 43,197 | 1.0314 | 6.2 | 500 | 26 | 160 | 95 | 730 | 26,717 |
| 7 | B | 37,488 | 1.027 | 6.4 | 473 | 21 | 138 | 42 | 652 | 22,984 |
| 8 | C | 76,942 | 1.0542 | 6.8 |  | 49 | 343 | 365 | 1,656 | 46,274 |
| 9 | D | 57,638 | 1.0407 | 6.2 | 671 | 28 | 160 | 120 | 2,450 | 35,260 |
| 10 | E | 67,532 | 1.0467 | 6.7 | 230 |  | 26 | n.a. | 1,105 | 42,365 |
| 11 | E | 23,742 | 1.0281 | 7.3 | 1,618 |  | <1 | n.a. | 35 | 20,476 |
| 12 | F | 55,696 | 1.0336 | 7.0 | 697 | 24 | 93 | 200 | 1,096 | 29,273 |
| 13 | F |  |  |  |  |  |  |  |  |  |
| 14 | F | 65,924 | 1.0426 | 7.1 | 1,104 | 19 | 8 | 170 | 802 | 33,411 |
| 15 | G | 38,676 | 1.0294 | 6.5 | 805 | 40 | 79 | 121 | 1,041 | 24,615 |
| 16 | H | 147,451 | 1.0827 | 5.9 | 0 | 30 | 953 | 139 | 14,014 | 95,339 |
| 17 | I | 39,200 | 1.0301 | 6.1 | 866 | 34.89 | 88 | 106 | 1,720 | 24,886 |
| 18 | J | 75,598 | 1.0558 | 6.2 | 638 | 46 | 238 | 232 | 3,732 | 47,930 |
| 19 | K | 80,814 | 1.0546 | 5.4 | 561 | 45 | 238 | 185 | 3,304 | 53,302 |
| 20 | L | 36,044 | 1.0275 | 6.7 | 1,164 | 12 | 36 | 295 | 500 | 22,140 |
| 21 | L | 36,018 | 1.0277 | 6.8 | 1,267 | 12 | 35 | 290 | 498 | 22,780 |
| 22 | L | 40,689 | 1.0279 | 6.9 | 1,441 | 11 | 30 | 265 | 430 | 22,838 |
| 23 | L | 48,438 | 1.0341 | 7.4 | 2,358 | 9 | 15 | 235 | 220 | 26,153 |

TABLE 1-continued

Dataset obtained from geochemical composition of produced water samples from formation X with one selected sample (No. 1, 5, 8-10, 12, 15-20, 25, 28, and 29) for each well (well No. A-O).

| Sample No. | Well No. | TDS [mg/L] | SG [g/cm$^3$] | pH | HCO$_3$ [mg/L] | B [mg/L] | Ba [mg/L] | Br [mg/L] | Ca [mg/L] | Cl [mg/L] |
|---|---|---|---|---|---|---|---|---|---|---|
| 24 | L | 46,563 | 1.0338 | 7.4 | 2,609 | 9 | 17 | 235 | 231 | 25,506 |
| 25 | M | 20,213 | 1.0152 | 5.8 | 610 | 64 | 39 | <10.00 | 487 | 12,519 |
| 26 | M | 11,161 | 1.0094 | 6.0 | 495 | 49 | 11 | <10.00 | 233 | 6,853 |
| 27 | M | 11,161 | 1.0094 | 6.0 | 495 | 49 | 11 | <10.00 | 233 | 6,853 |
| 28 | N | 152,972 | 1.1104 | 5.7 | 165 | <10 | 3,323 | 587 | 6,306 | 98,102 |
| 29 | O | 180,546 | 1.1309 | 5.3 | 72 | 7 | 2,133 | 842 | 9,084 | 115,550 |

TABLE 2

Dataset obtained from geochemical composition of produced water samples from formation X with one selected sample (No. 1, 5, 8-10, 12, 15-20, 25, 28, and 29) for each well (well No. A-O).

| Sample No. | Well No. | Fe [mg/L] | I [mg/L] | K [mg/L] | Li [mg/L] | Mg [mg/L] | Na [mg/L] | Si [mg/L] | Sr [mg/L] | SO$_4$ [mg/L] |
|---|---|---|---|---|---|---|---|---|---|---|
| 1 | A |  | 8.63 | 726 | 7.2 | 13 | 5,606 | 94 | 13 | 14 |
| 2 | A | 4 | <20 | 273 | 9 | 10 | 5,288 | 57 | 10 | 182 |
| 3 | A | <1 | <20 | 227 | 9.5 | 11 | 5,824 | 86 | 12 | 13 |
| 4 | A | 3 | <20 | 42970 | <0.1 | 105 | 371 | 15 | <1 | 66 |
| 5 | B | 4 | 68.9 | 498 | 30 | 42 | 15,649 | 65 | 157 | <100 |
| 6 | B | 3 | 67.1 | 490 | 30 | 40 | 15,110 | 63 | 156 | <100 |
| 7 | B | 2 | 63.1 | 444 | 25 | 36 | 13,243 | 55 | 135 | <100 |
| 8 | C | <1 | 4.61 | 1726 | 53 | 91 | 28,433 | 53 | 512 | 19 |
| 9 | D | 14 | 128 | 288 | 32 | 128 | 19,109 | 62 | 190 | <20 |
| 10 | E |  |  | 1590 |  | 59 | 23,765 |  | <1 | 8 |
| 11 | E |  |  | 22071 |  | <1 | 1,238 |  | <1 | 374 |
| 12 | F | <1 | 129 | 202 | 34 | 75 | 17,822 | 79 | 148 | 259 |
| 13 | F |  | 28 |  |  |  |  |  |  |  |
| 14 | F | 8 | 96.6 | 163 | 23 | 55 | 21,481 | 88 | 99 | 1153 |
| 15 | G | 40 |  | 261 | 36 | 40 | 12,075 | 98 | 144 | <100 |
| 16 | H | 104 |  | 369 | 55 | 656 | 37,342 | 42 | 55 | <100 |
| 17 | I |  |  | 146 |  | 89 | 11,539 |  | 127 | <100 |
| 18 | J | 27 | 177 | 256 | 63 | 207 | 23,072 | 23 | 574 | <20 |
| 19 | K | 6 | 171 | 299 | 65 | 178 | 23,369 | 77 | 528 | <100 |
| 20 | L | 4 |  | 304 | 19 | 58 | 12,030 |  | 62 | 152 |
| 21 | L | 3 |  | 299 | 19 | 56 | 11,258 |  | 60 | 159 |
| 22 | L | 2 |  | 276 | 17 | 50 | 15,742 |  | 54 | 188 |
| 23 | L | <1 |  | 297 | 14 | 33 | 19,043 |  | 36 | 631 |
| 24 | L | 1 |  | 303 | 15 | 34 | 17,572 |  | 39 | 611 |
| 25 | M | 101 | 30.5 | 667 | 13 | 41 | 6,530 | 102 | 60 | 26 |
| 26 | M | 128 | 20.1 | 972 | 8 | 26 | 3,514 | 100 | 24 | 40 |
| 27 | M | 128 | 20.1 | 972 | 8 | 26 | 3,514 | 100 | 24 | 40 |
| 28 | N | <1 |  | 1164 | 40 | 817 | 47,482 | 20 | 1,781 | <100 |
| 29 | O | 44 | <100 | 1284 | 28 | 1,506 | 54,234 | 24 | 706 | <100 |

TABLE 3A

Dataset obtained from geochemical composition of produced water samples from formation X with one selected sample (No. 1, 5, 8-10, 12, 15-20, 25, 28, and 29) for each well (well No. A-O).

| Sample No. | Well No. | δ$^{18}$O [‰] | Stdv [‰] | δ$^2$H [‰] | Stdv [‰] | δ$^{13}$C [‰] | $^{14}$C [pmC] | ± [pmC] | $^{14}$C age [yrBP] | ± [yrBP] |
|---|---|---|---|---|---|---|---|---|---|---|
| 1 | A | -2.66 | 0.13 | -41.70 | 0.50 | 0.00 | 69.33 | 0.24 | 2,942 | 27 |
| 2 | A | -1.49 | 0.15 | -34.50 | 0.30 | -5.19 |  |  |  |  |
| 3 | A | -2.33 | 0.15 | -38.80 | 0.40 | -5.01 | 61.55 | 0.21 | 3,899 | 27 |
| 4 | A | -4.45 | 0.12 | -47.60 | 0.30 | 0.41 | 13.66 | 0.09 | 15,990 | 53 |
| 5 | B | -0.89 | 0.07 | -31.87 | 0.30 | 2.80 | 0.81 | 0.05 | 38,736 | 465 |
| 6 | B | -1.20 | 0.02 | -31.95 | 0.19 | 2.35 | 0.85 | 0.05 | 38,318 | 469 |
| 7 | B | -1.66 | 0.09 | -32.15 | 0.20 | 4.00 | 1.71 | 0.05 | 32,670 | 222 |
| 8 | C | -0.92 | 0.12 | -29.50 | 0.30 | 1.51 | 3.15 | 0.05 | 27,789 | 132 |
| 9 | D | -0.70 | 0.06 | -31.91 | 0.22 | 10.80 | 2.06 | 0.06 | 31,180 | 227 |
| 10 | E | -1.00 | 0.06 | -33.92 | 0.20 | 1.30 | 11.78 | 0.10 | 17,181 | 68 |
| 11 | E | -4.41 | 0.12 | -45.48 | 0.18 | -3.15 | 10.07 | 0.09 | 18,443 | 73 |

TABLE 3A-continued

Dataset obtained from geochemical composition of produced water samples from formation X with one selected sample (No. 1, 5, 8-10, 12, 15-20, 25, 28, and 29) for each well (well No. A-O).

| Sample No. | Well No. | $\delta^{18}O$ [‰] | Stdv [‰] | $\delta^2H$ [‰] | Stdv [‰] | $\delta^{13}C$ [‰] | $^{14}C$ [pmC] | ± [pmC] | $^{14}C$ age [yrBP] | ± [yrBP] |
|---|---|---|---|---|---|---|---|---|---|---|
| 12 | F | -0.40 | 0.05 | -31.51 | 0.32 | 5.37 | 9.15 | 0.00 | 19,120 | 53 |
| 13 | F | -0.56 | 0.07 | -32.64 | 0.41 | 4.65 | 7.61 | 0.00 | 20,691 | 53 |
| 14 | F | -2.10 | 0.02 | -39.19 | 0.20 | 7.41 | 3.82 | 0.00 | 26,227 | 1 |
| 15 | G | 0.39 | 0.03 | -34.7 | 0.1 | 3.9 | 2.74 | 0.2 | 28,905 | 580 |
| 16 | H | 0.03 | 0.07 | -37.5 | 0.2 | 16.2 | 13.98 | 0.28 | 15,805 | 160 |
| 17 | I | -1.07 | 0.07 | -34.5 | 0.2 | 11.3 | 20.74 | 0.34 | 12,635 | 131 |
| 18 | J | 0.51 | 0.07 | -35.2 | 0.4 | 7.6 | 32.58 | 0.26 | 9,009 | 64 |
| 19 | K | 0.57 | 0.03 | -34.1 | 0.3 | 14.6 | 16.35 | 0.23 | 14,546 | 111 |
| 20 | L | -5.42 | 0.05 | -45.80 | 0.40 | -10.50 | | | | |
| 21 | L | | | | | -10.50 | 6.61 | 0.07 | 21,822 | 85 |
| 22 | L | -5.44 | 0.07 | -46.80 | 0.40 | -11.75 | | | | |
| 23 | L | -6.23 | 0.06 | -51.80 | 0.20 | -10.80 | | | | |
| 24 | L | | | | | -11.75 | 7.93 | 0.07 | 20,360 | 71 |
| 25 | M | -7.66 | 0.12 | -31.78 | 0.19 | -1.10 | 42.01 | 0.18 | 6,967 | 34 |
| 26 | M | 4.15 | 0.00 | -12.15 | 0.28 | 2.75 | 18.76 | 0.12 | 13,443 | 51 |
| 27 | M | 4.15 | 0.00 | -12.15 | 0.28 | 2.75 | 18.76 | 0.12 | 13,443 | 51 |
| 28 | N | -2.76 | 0.01 | -37.3 | 0.1 | 13 | 2.49 | 0.34 | 29,681 | 1,085 |
| 29 | O | -2.83 | 0.07 | -31 | 0.3 | -17.7 | | | | |

TABLE 3B

Dataset obtained from geochemical composition of produced water samples from formation X with one selected sample (No. 1, 5, 8-10, 12, 15-20, 25, 28, and 29) for each well (well No. A-O).

| Sample No. | Well No. | $\delta^{18}O_{SO4}$ [‰] | $\delta^{34}O_{SO4}$ [‰] | $\delta^{37}Cl$ [‰] | Stdv [‰] | $^{11}B/^{10}B$ [‰] | $^{81}Br/^{79}Br$ [‰] | Stdv [‰] |
|---|---|---|---|---|---|---|---|---|
| 1 | A | 20.7 | 23.7 | -0.61 | 0.07 | -4.4 | 0.41 | 0.06 |
| 2 | A | | | | | | | |
| 3 | A | 18.7 | 20.5 | | | | | |
| 4 | A | 12.8 | 13.9 | | | | | |
| 5 | B | 19.7 | 15.4 | | | | | |
| 6 | B | | | | | | | |
| 7 | B | | | | | 30.1 | 1.43 | 0.08 |
| 8 | C | | | 0.28 | 0.10 | 30.2 | 0.74 | 0.12 |
| 9 | D | 25.2 | 9.2 | | | | | |
| 10 | E | 28.6 | 16.9 | -0.50 | 0.15 | 27.5 | | |
| 11 | E | 5.7 | 1.4 | -0.58 | 0.06 | 21.0 | | |
| 12 | F | 10.0 | 1.5 | -0.73 | 0.10 | | | |
| 13 | F | 10.2 | 2.05 | -0.61 | 0.10 | | | |
| 14 | F | 10.3 | 1.8 | -0.41 | 0.12 | | | |
| 15 | G | | | | | | | |
| 16 | H | | | | | 24.1 | | |
| 17 | I | | | | | 20.8 | | |
| 18 | J | | | | | 21.8 | | |
| 19 | K | | | | | 20.85 | | |
| 20 | L | | | | | | | |
| 21 | L | | | | | | | |
| 22 | L | | | | | | | |
| 23 | L | | | | | | | |
| 24 | L | | | | | | | |
| 25 | M | 10.1 | 9.4 | -1.73 | 0.14 | -1.6 | -0.06 | 0.08 |
| 26 | M | 7.0 | 14.7 | -1.81 | 0.10 | 1.0 | -0.88 | 0.1 |
| 27 | M | 7.0 | 14.7 | -1.81 | 0.10 | 1.0 | -0.88 | 0.1 |
| 28 | N | | | | | 26 | | |
| 29 | O | | | | | 40.6 | | |

TABLE 3C

Dataset obtained from geochemical composition of produced water samples from formation X with one selected sample (No. 1, 5, 8-10, 12, 15-20, 25, 28, and 29) for each well (well No. A-O).

| Sample No. | Well No. | $^{87}Sr/^{86}Sr$ | Stdv | $^{36}Cl/Cl$ [$10^{-15}$] | Stdv [$10^{-15}$] | $^{36}Cl/L$ [$10^6$ at/L] | $^{129}I/I$ [$10^6$ at/L] | $^{129}I/^{127}I$ [$10^{-15}$] |
|---|---|---|---|---|---|---|---|---|
| 1 | A | 0.71692 | 0.000032 | 14.16 | 1.31 | 1947 | 15.7 | 384 |
| 2 | A | | | | | | | |
| 3 | A | 0.71678 | 0.000031 | | | | | |
| 4 | A | 0.71336 | 0.000039 | | | | | |
| 5 | B | 0.71782 | 0.000026 | | | | | |
| 6 | B | 0.71783 | 0.000024 | | | | | |
| 7 | B | 0.71784 | 0.000033 | | | | 42.6 | 142 |
| 8 | C | 0.71594 | 0.000027 | 12.00 | 1.51 | 9432 | 20.9 | 956 |
| 9 | D | 0.71706 | 0.000025 | | | | | |
| 10 | E | 0.71727 | 0.000103 | 7.69 | 0.7 | 5532 | | |
| 11 | E | 0.71403 | 0.000022 | 0.125 | 0.58 | 43 | | |
| 12 | F | 0.71700 | 0.000035 | 11.03 | 1.86 | 5483 | 41.8 | 1,195 |
| 13 | F | 0.71701 | 0.000031 | 9.33 | 3.67 | 4777 | 116 | 874 |
| 14 | F | 0.71699 | 0.000031 | | | | | |
| 15 | G | 0.7174727 | 0.000120 | | | | | |

TABLE 3C-continued

Dataset obtained from geochemical composition of produced water samples from formation X with one selected sample (No. 1, 5, 8-10, 12, 15-20, 25, 28, and 29) for each well (well No. A-O).

| Sample No. | Well No. | $^{87}Sr/^{86}Sr$ | Stdv | $^{36}Cl/Cl$ [$10^{-15}$] | Stdv [$10^{-15}$] | $^{36}Cl/L$ [$10^6$ at/L] | $^{129}I/I$ [$10^6$ at/L] | $^{129}I/^{127}I$ [$10^{-15}$] |
|---|---|---|---|---|---|---|---|---|
| 16 | H | 0.7170155 | 0.000076 | | | | | |
| 17 | I | 0.7170793 | 0.000118 | | | | | |
| 18 | J | 0.7172741 | 0.000075 | | | | | |
| 19 | K | 0.7172471 | 0.000063 | | | | | |
| 20 | L | 0.716274 | 0.000030 | | | | | |
| 21 | L | | | | | | | |
| 22 | L | 0.716292 | 0.000039 | | | | | |
| 23 | L | 0.716284 | 0.000046 | | | | | |
| 24 | L | | | | | | | |
| 25 | M | 0.717352 | 0.000027 | 13.16 | 0.88 | 2798 | 15.2 | 105 |
| 26 | M | 0.717143 | 0.000030 | 10.58 | 0.85 | 1231 | 9.83 | 103 |
| 27 | M | 0.717143 | 0.000030 | 10.58 | 0.85 | 1231 | 9.83 | 103 |
| 28 | N | 0.7188344 | 0.000113 | | | | | |
| 29 | O | 0.7220861 | 0.000084 | | | | | |

In step 308, the dataset is analyzed using principal component analysis (PCA) to obtain the principal components of the dataset. PCA is used as a multivariate statistical technique to partition and to reduce the dimensions of the dataset.

The original dataset contains a large number of elements. For analyzing the large dataset, the dimensions are reduced to principal components. The number of principal components is chosen based on the elbow method which basically uses the scree plot to determine where the biggest drop in proportion of variance explained occurs. The plot and the PCA reduction have been performed using the sklearn decomposition library in python.

The purpose of PCA is to transform a large dataset of geochemical compositions to principal components. Each principal component is a linear combination of all the geochemical compositions weighted with factors of the principal components according to their eigenvectors. The number of principal components is chosen and may be up to the total number of the original geochemical compositions in the dataset.

Table 4 and 5 show a dataset with 13 geochemical components and four principal components of 15 selected water samples.

TABLE 4

Dataset of 13 geochemical components and four principal components of 15 selected water samples.

| Well | Predicted Labels [after PCA] | PC_4 | PC_3 | PC_2 | PC_1 | Mg | Ca | Sr | Ba |
|---|---|---|---|---|---|---|---|---|---|
| A | 1 | 1.1981 | 1.5319 | 3.2096 | −3.1835 | 13 | 144 | 13 | 9 |
| B | 2 | −0.6856 | −1.5856 | −0.8400 | −0.7651 | 42 | 749 | 157 | 160 |
| C | 2 | 0.3248 | −2.8292 | −0.8482 | −0.6229 | 91 | 1,656 | 512 | 343 |
| D | 3 | −0.0793 | 0.1443 | −1.2723 | −0.6555 | 128 | 2,450 | 190 | 160 |
| E | 3 | −1.2934 | 0.2422 | −0.5379 | −0.9966 | 59 | 1,105 | 252 | 26 |
| F | 3 | −0.3603 | −0.7680 | −0.3501 | −1.2204 | 75 | 1,096 | 148 | 93 |
| G | 3 | −0.3705 | −0.4181 | −1.1888 | −1.0777 | 40 | 1,041 | 144 | 79 |
| H | 4 | 0.3499 | 3.2143 | −1.7995 | 2.3038 | 656 | 14,014 | 55 | 953 |
| I | 5 | 0.2306 | 0.9396 | −1.0071 | −0.8851 | 89 | 1,720 | 127 | 88 |
| J | 5 | 0.8028 | 0.3494 | −0.2313 | −0.0404 | 207 | 3,732 | 574 | 238 |
| K | 5 | 1.1631 | 0.3609 | −1.2184 | 0.3427 | 178 | 3,304 | 528 | 238 |
| L | 6 | −1.4653 | −0.4713 | 1.9447 | −1.7867 | 58 | 500 | 62 | 36 |
| M | 6 | 0.1388 | 0.5325 | 1.2265 | −2.1596 | 41 | 487 | 60 | 39 |
| N | 7 | 2.1947 | −1.7468 | 1.3568 | 4.8614 | 817 | 6,306 | 1,781 | 3,323 |
| O | 8 | −2.1483 | 0.5040 | 1.5561 | 5.8855 | 1,506 | 9,084 | 706 | 2,133 |

TABLE 5

Dataset of 13 geochemical components and four principal components of 15 selected water samples.

| Well | Predicted Labels [after PCA] | $^2H$ | $^{87}Sr/^{86}Sr$ | $^{13}C$ | $^{14}C$ | $^{11}B/^{10}B$ | Sr/Ca | Na/Cl | Mg/Ca | TDS |
|---|---|---|---|---|---|---|---|---|---|---|
| A | 1 | −41.7 | 0.716920 | 5.3 | 69.3 | −4.4 | 0.090278 | 0.69227 | 0.0903 | 16,606 |
| B | 2 | −31.9 | 0.717815 | 2.8 | 0.8 | 29.8 | 0.209613 | 0.558833 | 0.0561 | 46,100 |
| C | 2 | −29.5 | 0.715938 | 1.5 | 3.1 | 30.2 | 0.309179 | 0.614449 | 0.0550 | 80,050 |
| D | 3 | −31.9 | 0.717063 | 10.8 | 2.1 | 20.0 | 0.077551 | 0.541946 | 0.0522 | 58,646 |

TABLE 5-continued

Dataset of 13 geochemical components and four principal components of 15 selected water samples.

| Well | Predicted Labels [after PCA] | $^2$H | $^{87}$Sr/$^{86}$Sr | $^{13}$C | $^{14}$C | $^{11}$B/$^{10}$B | Sr/Ca | Na/Cl | Mg/Ca | TDS |
|---|---|---|---|---|---|---|---|---|---|---|
| E | 3 | −33.9 | 0.717273 | 1.3 | 11.8 | 27.5 | 0.000452 | 0.560958 | 0.0534 | 69,155 |
| F | 3 | −31.5 | 0.717003 | 5.4 | 9.2 | 20.9 | 0.135036 | 0.60882 | 0.0684 | 50,138 |
| G | 3 | −33.0 | 0.717473 | 3.9 | 2.7 | 20.9 | 0.138329 | 0.490555 | 0.0384 | 39,395 |
| H | 4 | −37.5 | 0.717016 | 16.2 | 14.0 | 24.1 | 0.003925 | 0.391676 | 0.0468 | 149,249 |
| I | 5 | −34.5 | 0.717079 | 11.3 | 20.7 | 20.8 | 0.073837 | 0.463674 | 0.0517 | 39,461 |
| J | 5 | −35.2 | 0.717274 | 7.6 | 32.6 | 21.8 | 0.153805 | 0.481369 | 0.0555 | 77,215 |
| K | 5 | −34.1 | 0.717247 | 14.6 | 16.4 | 20.9 | 0.159806 | 0.438426 | 0.0539 | 82,328 |
| L | 6 | −45.8 | 0.716274 | −10.5 | 6.6 | 20.9 | 0.124 | 0.54336 | 0.1160 | 36,776 |
| M | 6 | −31.8 | 0.717352 | −1.1 | 42.0 | −1.6 | 0.123203 | 0.521607 | 0.0842 | 21,259 |
| N | 7 | −37.3 | 0.718834 | 13.0 | 2.5 | 26.0 | 0.282429 | 0.484006 | 0.1296 | 152,972 |
| O | 8 | −31.0 | 0.722086 | 5.3 | 17.8 | 40.6 | 0.077719 | 0.469355 | 0.1658 | 185,519 |

Table 6 shows the eigenvalues (column 2) determined for each of the principal components (column 1), and their corresponding variance percentage (column 3). The variance percentage describes how much of the total variance is explained by each of the principal components with respect to the cumulative variance.

TABLE 6

Principal components and their eigenvalues and the percentage of variance of the eigenvalues that contribute to each principal component.
Eigenvalues & Variance Explained

| Component | Eigenvalue | Percent of Variance | Cumulative Eigenvalue | Cumulative Percent of Variance |
|---|---|---|---|---|
| 1 | 6.32 | 45.58% | 6.32 | 45.58% |
| 2 | 2.37 | 17.06% | 8.69 | 62.64% |
| 3 | 1.87 | 13.47% | 10.55 | 76.11% |
| 4 | 1.20 | 8.66% | 11.76 | 84.77% |
| 5 | 0.92 | 6.63% | 12.67 | 91.40% |
| 6 | 0.52 | 0.037648 | 13.20 | 95.16% |
| 7 | 0.28 | 0.02044 | 13.48 | 97.21% |
| 8 | 0.17 | 0.012559 | 13.65 | 98.46% |
| 9 | 0.12 | 0.008551 | 13.77 | 99.32% |
| 10 | 0.06 | 0.004259 | 13.83 | 99.75% |
| 11 | 0.03 | 0.001914 | 13.86 | 99.94% |
| 12 | 0.01 | 0.000371 | 13.86 | 99.97% |
| 13 | 0.00 | 0.000264 | 13.87 | 100.00% |

However, based on the analysis of the eigenvalues and the percentages of variance associated with each factor, the number of factors retained may be chosen based on the needed variability of the percentage of variance the reduced data. In this case, four components are chosen which correspond to 84.77% of variance. This means that 84.77% of the data is explained when the dataset is reduced to four components. The analysis was performed on water samples exclusively from formation X to examine the lateral communication between the different hydrodynamic groups.

According to a criterion, factors with eigenvalues that exceed one should be retained which in this case are the first four components. These four factors correspond to a cumulative variance of 84.77% which means reducing the dimensions of the data to four components would explain 84.77% of the data. The contribution of each component is computed for each of the 15 wells.

As shown in table 6, the first principal component corresponds to 45.58%, the second principal component explains approximately 17.06% of the data, the third principal component explains 13.47% of the data, and the fourth principal component explains about 8.66% of the data. All four principal components explain 84.77% of the total variance.

This describes the reduction of the dimensions in the dataset and how the number of components correspond to a specific variance. As shown in table 6, reducing the dataset to four components corresponds to accommodating and analyzing 84.77% of the data. The variance percentage basically represents how much of the total variance is explained by each of the PCs with respect to the cumulative variance.

It is expected that the first factor is more correlated with the variables than the second, third, and fourth factors since factors are extracted successively, each one accounting for as much of the remaining variance as possible.

After reducing the dimensions of the dataset to principal components, four in this case, the principal components are clustered.

In step 310, the principal components are grouped to obtain clusters. In one or more embodiments, the principal components are clustered by k-means clustering.

Table 7 shows the four principal components, PC_1, PC_2, PC_3, PC_4, and the result of the k-means clustering in the column labelled "Post PCA K-Means Labels" for each well A-O in this particular example. The k-means clustering identified 8 different clusters as shown in column "Post PCA K-Means Labels".

TABLE 7

Factors for the principal components for each of the wells.
Principal Component Factors & K-Means Clusters

| Well | Post PCA k-means Labels | PC_1 | PC_2 | PC_3 | PC_4 |
|---|---|---|---|---|---|
| K | 1 | 0.34 | −1.22 | 0.36 | 1.16 |
| J | 1 | −0.04 | −0.23 | 0.35 | 0.80 |
| I | 1 | −0.89 | −1.01 | 0.94 | 0.23 |
| O | 2 | 5.89 | 1.56 | 0.50 | −2.15 |
| M | 3 | −2.16 | 1.23 | 0.53 | 0.14 |
| L | 3 | −1.79 | 1.94 | −0.47 | −1.47 |
| G | 4 | −1.08 | −1.19 | −0.42 | −0.37 |
| E | 4 | −1.00 | −0.54 | 0.24 | −1.29 |
| F | 4 | −1.22 | −0.35 | −0.77 | −0.36 |
| D | 4 | −0.66 | −1.27 | 0.14 | −0.08 |
| N | 5 | 4.86 | 1.36 | −1.75 | 2.19 |
| H | 6 | 2.30 | −1.80 | 3.21 | 0.35 |
| A | 7 | −3.18 | 3.21 | 1.53 | 1.20 |
| C | 8 | −0.62 | −0.85 | −2.83 | 0.32 |
| B | 8 | −0.77 | −0.84 | −1.59 | −0.69 |
| | Variance Explained | 45.58% | 17.06% | 13.47% | 8.66% |

Figure 4:
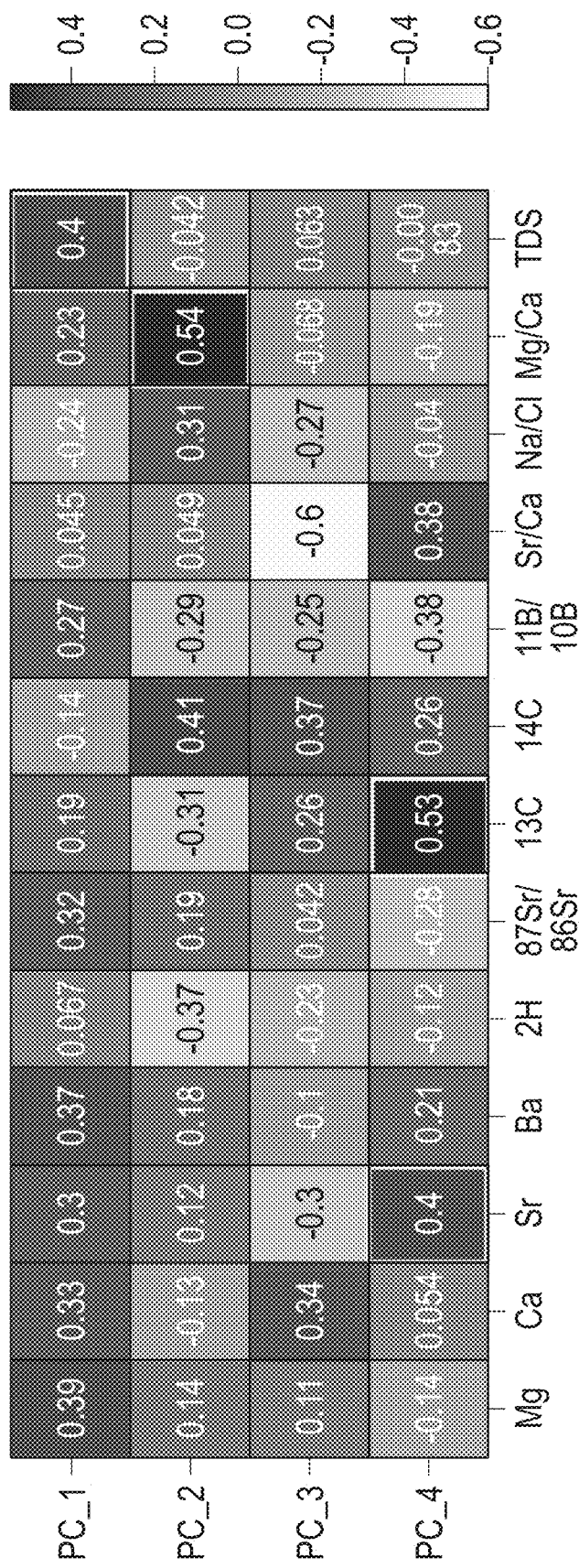
FIG. 4 shows a heat map of factor loadings which explain how the variables contributed to each of the principal components for the studied samples, according to one or more embodiments.

FIG. 4 shows a heat map created to demonstrate the loadings for each of the factor of the principal component.

The loadings describe how much each factor contributes to a particular principal component. Large loadings, positive or negative, indicate that a particular factor has a strong relationship to a particular principal component. The sign of a loading indicates whether a factor and a principal component are positively or negatively correlated.

As shown in FIG. 4, TDS has the highest positive loading on the first principal component which explains nearly 45.58% of the data. The second principal component explains approximately 17% of the total variance and has the strongest positive loading for Ca/Mg and $^{14}$C which complements the combined approach of the hydro-chemical ratios (Na/Cl vs. Ca/Mg) with TDS and carbon-14 ages that facilitated the differentiation of different water types and their assignment to hydrodynamic groups. The third principal component explains 13.47% of the data and has the strongest negative loading for Sr/Ca.

Figure 5:
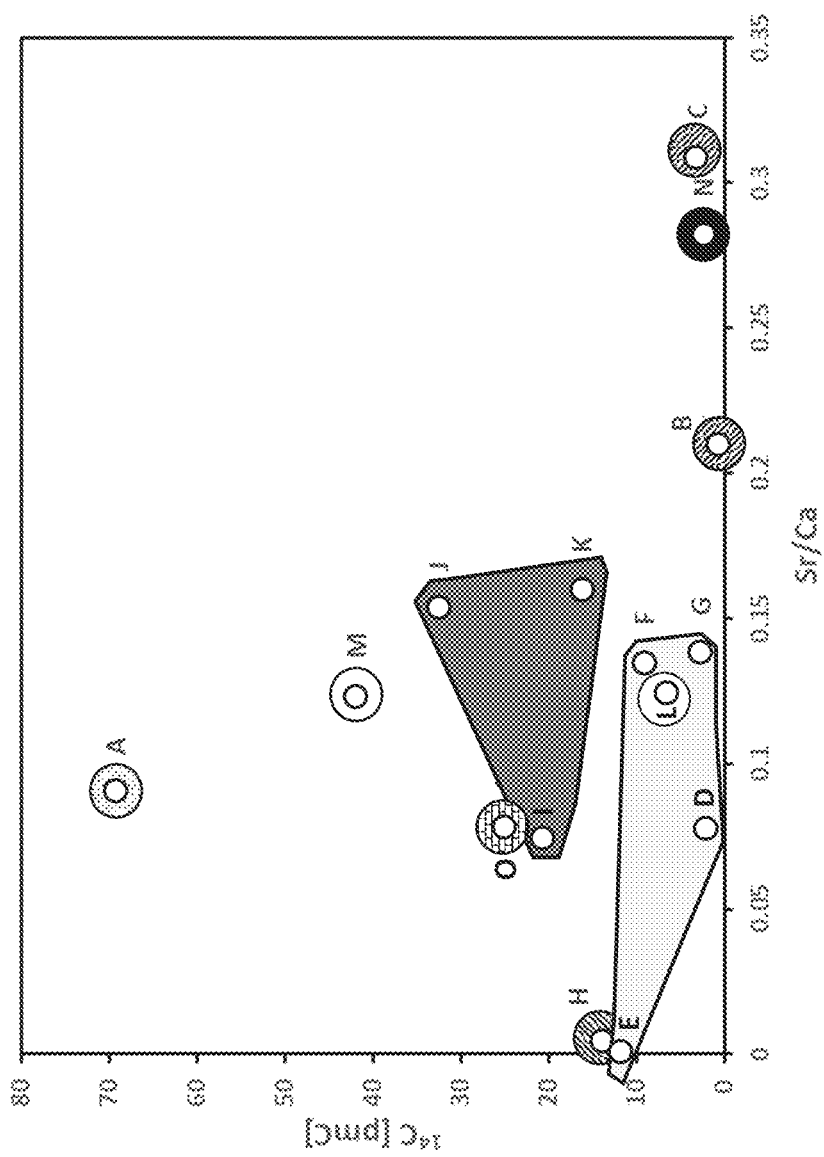
FIG. 5 shows the Sr/Ca ration vs. $^{14}$C concentration in the formation water samples in context to their labeled clusters, according to one or more embodiments.
Figure 6:
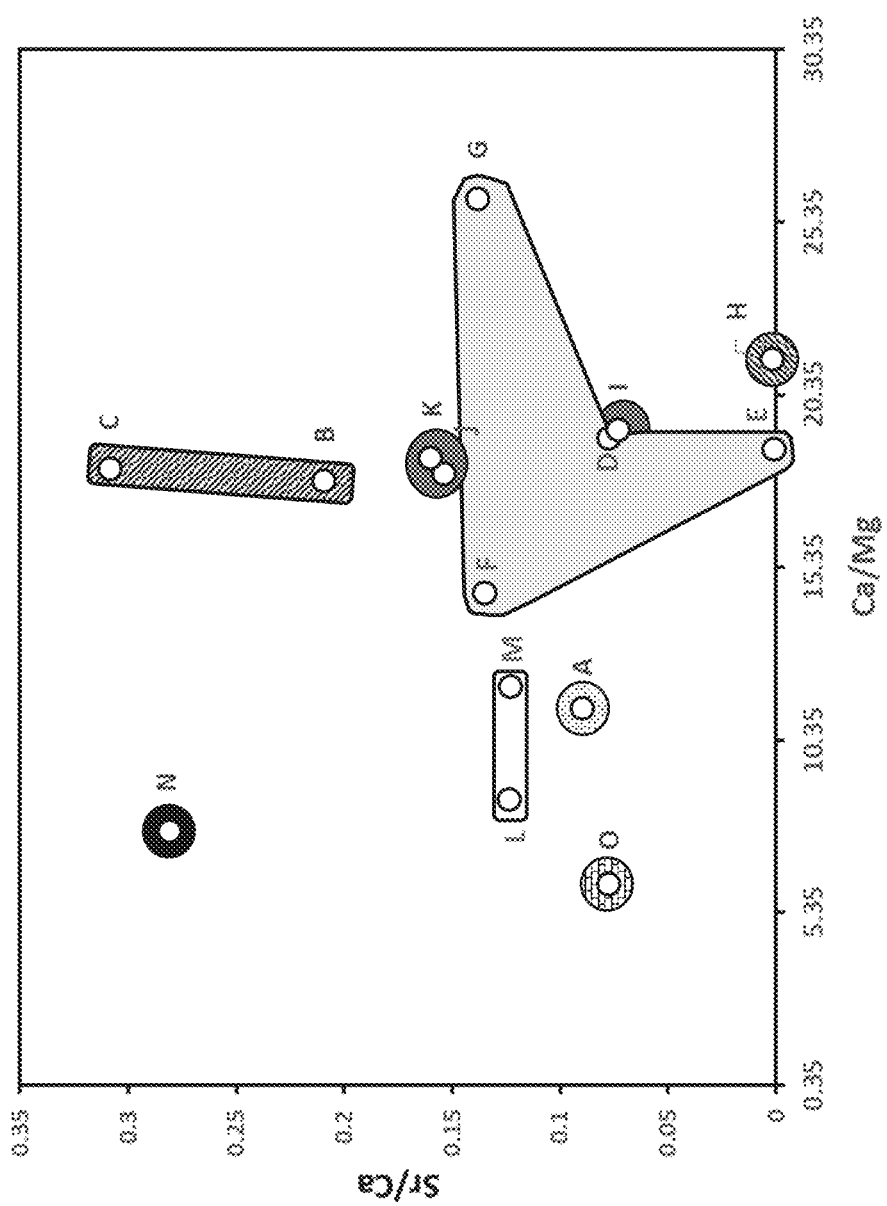
FIG. 6 shows the Ca/Mg ration vs. Sr/Ca ration of the formation water samples in context to their labeled clusters, according to one or more embodiments.

FIG. 5 shows a plot of Sr/Ca vs. $^{14}$C and FIG. 6 shows a plot of Ca/Mg vs. Sr/Ca for each of the wells A-O. The plotting of different concentrations and ratios is required to visualize the presence of different water types, which were assigned to distinct clusters and hydrodynamic groups.

As seen in the plots of FIG. 5 and FIG. 6, water sample correlations are mainly consistent with the labeled clusters. The fourth principal component is considerably less significant since it explains about 8.6% of the data, as shown in table 6. However, it is essential to note that it has the high positive loadings for $\delta^{13}$C and Sr. Isotopic concentrations such as $\delta^{13}$C play a key role in grouping the different hydrodynamic groups. Formation water from well H in hydrodynamic group 4 and well O in hydrodynamic group 8, for example, have very distinct values of $\delta^{13}$C, the highest of 16.2% and lowest of 3.8%, respectively. These $\delta^{13}$C ratios majorly contribute to identifying each of the two wells as separate hydrodynamic groups.

In step 312, hydrodynamic groups are identified from the clusters.

The clustering resulted in eight different clusters that are the hydrodynamic groups identified in the sedimentary unit of Formation X within a specific exploration area. A hydrodynamic group is the opposite of a hydrostatic group and is defined as an entity of a fluid body in local equilibrium, which is in motion. The flow may be smooth and steady laminar flow or unsettled and disturbed turbulent flow.

In step 314, the wells are assigned to hydrodynamic groups, wherein wells within one single hydrodynamic group are considered to be hydraulically communicated or coupled. In other words, wells within one single hydrodynamic group are fluidly connected to each other.

Figure 7:
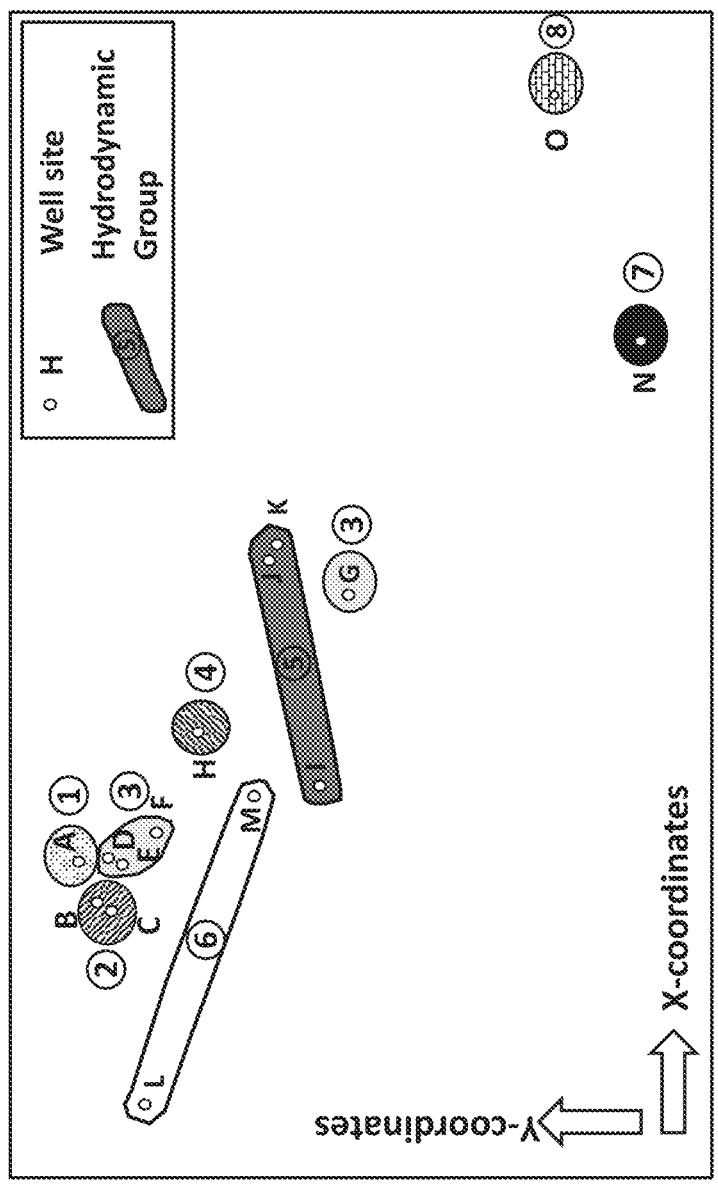
FIG. 7 shows a distribution map of exploration wells and their assignment to different statistical hydrodynamic groups, according to one or more embodiments.

FIG. 7 shows the location and spatial distribution of wells A to O classified as exploration wells and their assignment to defined hydrodynamic groups within the formation X. As shown in FIG. 7, well A belongs to a first hydrodynamic group 1, wells B and C belong to a second hydrodynamic group 2, wells D, E, and F belong to a third hydrodynamic group 3, well H belongs to a fourth hydrodynamic group 4, wells I, and J belong to a fifth hydrodynamic group 5, wells L, and M belong to a sixth hydrodynamic group 6, well G belongs to the third hydrodynamic group of the wells D, E, and F, N belongs to a seventh hydrodynamic group 7, and well O belongs to an eighth hydrodynamic group 8.

Figure 8:
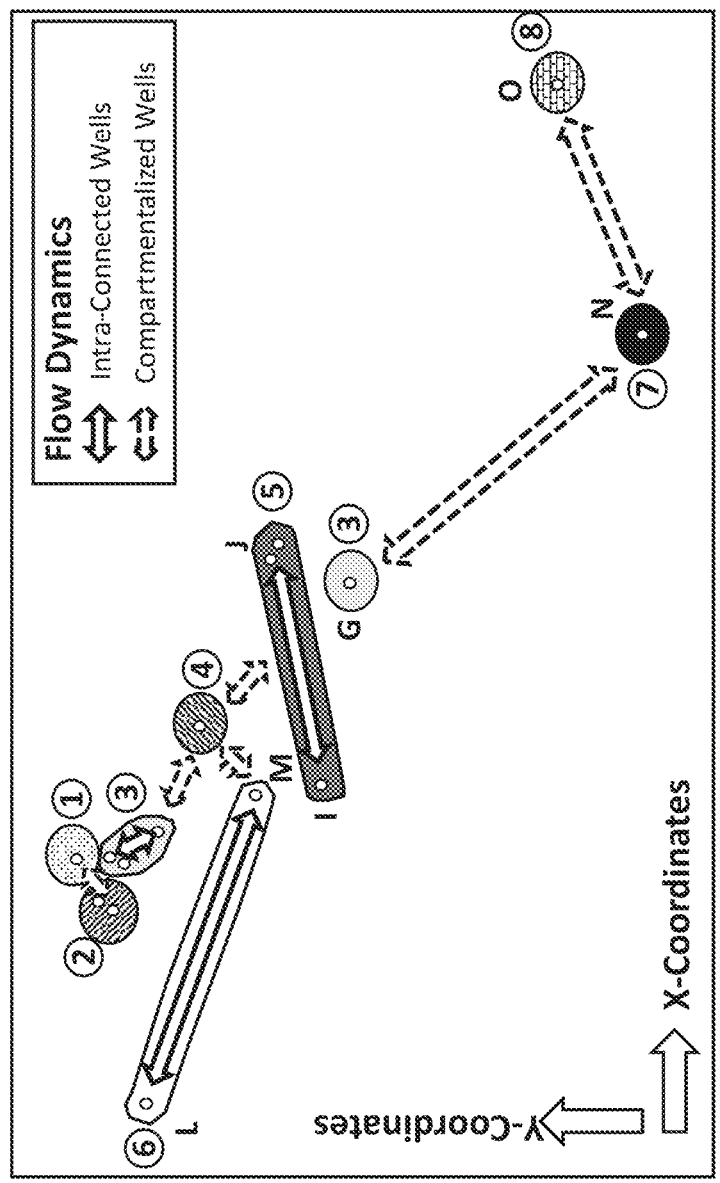
FIG. 8 shows a migration model with interpreted pathways within each hydrodynamic group, interpreted location of barriers between hydrodynamic with limited flow circulation, according to one or more embodiments.

FIG. 8 shows wells within one single hydrodynamic group that are hydraulically connected and may therefore be interpreted as part of existing connected pathways. In contrast, hydrodynamic groups with distinct geochemical characteristics are interpreted to be compartmentalized wells.

As can be seen, wells L, and M of the sixth hydrodynamic group 6 are intra-connected wells, illustrated by solid arrows. Furthermore, the wells I, and J of the fifth hydrodynamic group 5 are also intra-connected wells. However, the wells G, N, and O are compartmentalized wells illustrated by dashed arrows.

Figure 9:
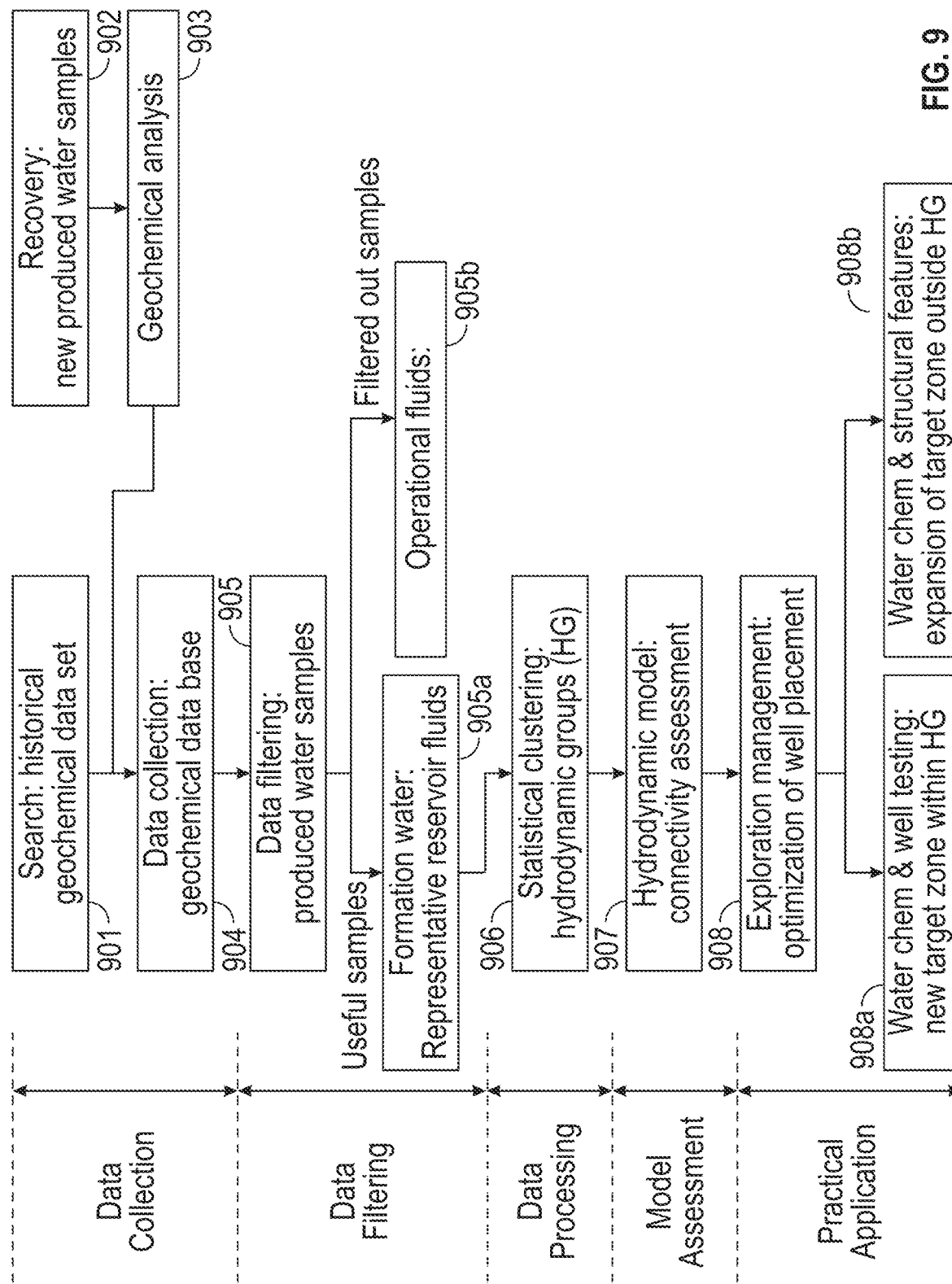
FIG. 9 shows another flowchart of the method steps to assess reservoir continuity between single wells in an oilfield formation within a region with several petroleum reservoirs, according to one or more embodiments.

FIG. 9 shows a workflow for the assessment of reservoir connectivity with geochemical and structural data.

In step 901, a historical geochemical dataset is searched. The historical geochemical datasets have been obtained from produced water samples of single wells of the oilfield formation in the past and have been stored in a database. The database may be searched for an existing historical geochemical dataset that is large enough to represent the geochemical composition of the single wells. In case the existing historical geochemical dataset is not large enough to represent the geochemical composition of the single wells, more water samples need to be obtained from the single wells of the oilfield formation.

In step 902, additional produced water samples are obtained from each single wells of the oilfield formation. This step is performed in case there are little existing historical geochemical data.

In step 903, the geochemical composition of the additional produced water samples is analyzed. This step is performed according to step 306 of FIG. 3. The results of the geochemical analysis are stored in a present geochemical dataset.

In step 904, the historical geochemical dataset, and the present geochemical dataset are compiled into a geochemical dataset. This step is called the data collection step. The geochemical dataset may be stored in the database.

The compilation into the geochemical dataset is performed by collating the historical and present geochemical dataset and transforming the historical and present geochemical dataset into a format that is easily manipulated in preparation for further processing, such as data filtering as described in the next step.

In step 905, the data of the produced water samples are filtered (data filtering step). In the data filtering step, the data of useful samples are filtered out from data of useless samples by the following criteria.

In one or more embodiments, the collected geochemical data is filtered by applying filtering criteria to detect the potential contamination (elevated concentrations of potassium) of produced water and to select the most representative water sample from each well and reservoir.

In one or more embodiments, the filtering criteria for the data filtering step is based on a long-year expertise in fluid characterization and source identification, sample description from field records, well type and development from drilling records, observed anomalies and outliers of specific elemental concentrations and ratios from field reports, anomalies in concentration ratios, i.e., of K/Cl, or Ca/Na, oxidizing conditions (elevated concentrations of sulfate $SO_4$), surface water input (elevated concentrations of bicarbonate $HCO_3$), mud filtration contamination (elevated concentrations of potassium), pH (extremely alkaline or acid), abundance of characteristic elements for formation water, i.e., barium, iodine, strontium, ion balance smaller than 10%.

The geochemical dataset of 29 produced water samples from formation X and 15 exploration wells was screened and reduced to a total of 15 produced water samples for representative formation water samples (see Table 1). The following filtering criteria were applied to detect the potential contamination of produced water and to select the most representative water sample from each well and reservoir.

In other embodiments, the filtering criteria includes software codes with AI-based, supervised, and semi-supervised learning methods may be utilized to identify formation water samples and separate them from operation-related fluids, i.e., mud filtrate, completion brine, supply water, condensate water.

Useful samples represent formation water samples (step 905a) that are separated (filtered out) from production-related water types (operational fluids), such as mud filtrate, completion brine, supply water, condensate water, mixed water (step 905b).

Applicable methods are either the use of professional expertise in identifying water sources to detect anomalies in specific elemental concentrations and ratios in order to utilize sample descriptions from field reports, or to filter water types by specialized ML-software applications.

In step 906, statistical methods are applied to cluster the formation water samples from a specific lithological unit into hydrodynamic groups with similar geochemical properties. Hydrodynamic groups may be visualized as 2D maps.

As hydrodynamic groups are composed of inter-connected fluids as part of a dynamic groundwater system, the area of each hydrodynamic group and existing wells may be defined as an isolated, hydraulically connected reservoir complex (step 907).

In step 908, the spatial distribution of connected or isolated reservoir zones or blocks may be utilized as an exploration tool to reduce exploration risk by avoiding the drilling of dry holes. In detail, the size of exploration areas and drilling locations for new well sites may be optimized through an improved knowledge of migration pathways in the reservoir from geochemical data.

As a first step 908a, the hydrodynamic groups are coupled with pressure, volume, and temperature (PVT) testing data from individual wells classified as exploration wells. Exploration wells from one single hydrodynamic group are characterized by a homogeneous performance during PVT well testing. In that specific case, the exploration area may be extended throughout the entire area of the hydrodynamic group. The area of a specific hydrodynamic group with confirmed positive PVT testing of its respective exploration wells are fluidly connected, and therefore, the wells are considered to be hydraulically communicated. Thus, wells in a hydrodynamic group with positive PVT testing should be targeted for future drilling. In contrast, wells in hydrodynamic group areas with negative PVT testing are not fluidly connected, and therefore, are considered to be hydraulically compartmentalized. Thus, wells in a hydrodynamic group with negative PVT testing should be paused. Positive PVT criteria during well testing are the rate of produced hydrocarbons, initial pressure, and reservoir properties.

For coupling the hydrodynamic groups with PVT testing data, it is assumed that wells within one single hydrodynamic group are considered to be hydraulically communicated (e.g., fluidly connected) for an optimized assessment of drilling sites. The location of wells classified as exploration wells from a specific hydrodynamic group with positive results from well testing (regarding the nature and rate of produced fluids, initial pressure, and reservoir properties) may be utilized to assess potential sites for future exploration and drilling. The selection of new prospective areas is coupled to identified migration pathways between wells with optimum production properties.

Well-log derived PVT testing provides ambiguous interpretation regarding the hydraulic connectivity of the reservoirs and the presence of single or multi-layered systems. Different pressure and contact conditions are attributed to isolated reservoirs. On the other hand, unified pressure systems and oil/gas-water interfaces suggest conditions for a single reservoir, but separate geological traps testify their provenance to different reservoirs. The observation of initially equilibrated pressure conditions between different reservoir zones must not be conclusive for the presence of fluid connectivity during subsequent field operation. The main reason is that equilibrated pressure conditions may be formed through extended geologic time periods. On a geological time scale, pressure communication may be achieved between different reservoir compartments, but may deplete independently for each reservoir section during production.

The resolution of seismic surveys, even of high-resolution techniques, are limited to a grid cell size in the order of tens of meters for horizontal distances, and of several meters for vertical distances. The resolution is decreasing exponentially with depth.

With respect to organic data, samples and geochemical data of formation water are generally more abundant than analytical data from organic material.

Figure 10:
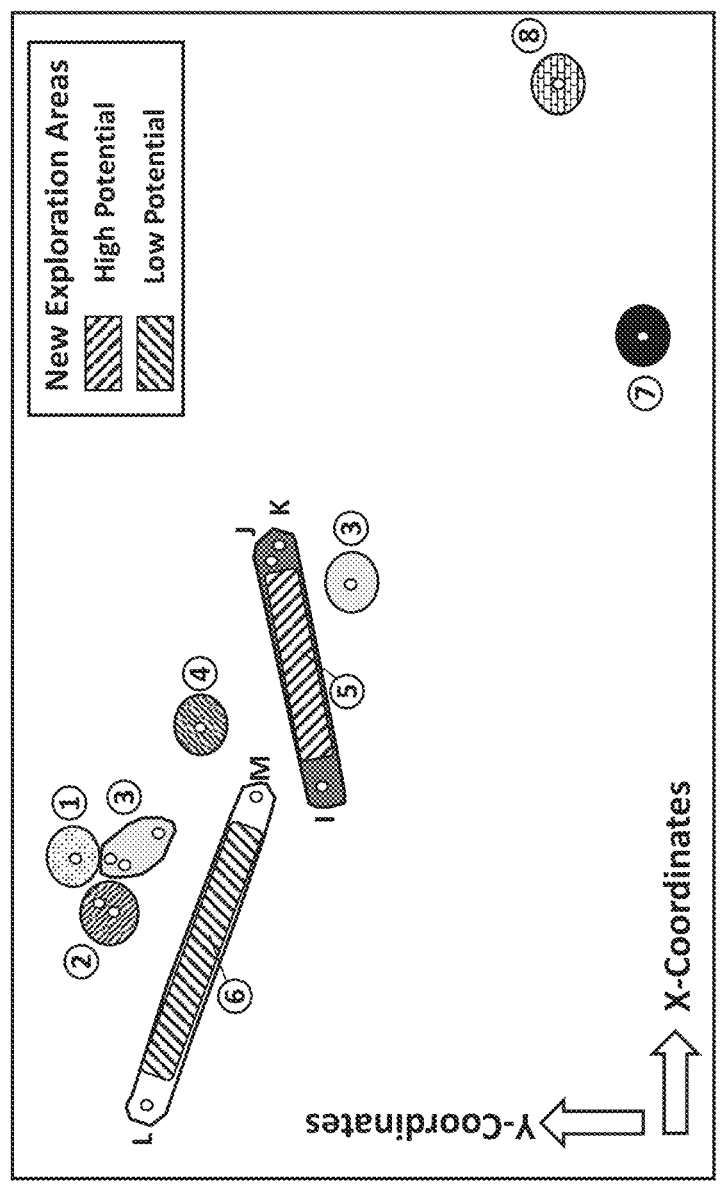
FIG. 10 shows a selection of potentially new drilling sites by an assessment of well testing data for each hydrodynamic group, according to one or more embodiments.

FIG. 10 shows an example of favorable testing conditions for the exploration wells I, J and K in hydrodynamic group 5 that suggest exploring for new prospection area between these wells in WSW-ENE direction (see dashed area inside hydrodynamic group 5), as indicated by detected fluid migration pathways in this direction. Exploration wells from group 5 showed elevated hydrocarbon presence during testing, and therefore the area in-between is classified as new drilling zone with high potential.

In contrast, hydrodynamically connected wells from hydrodynamic groups, but with low testing potential, should not be considered for further exploration strategies. As an example, wells L and M of the sixth hydrodynamic group 6 are hydrodynamically connected through an active groundwater system, but further exploration between both wells (see red area pattern) should not be proceeded due to a low testing productivity on hydrocarbons.

As a second step 908b, the location of structural features, such as fault, fractures, dikes, is utilized to define the spatial extension of potential exploration areas between hydrodynamic groups. The position of the structural features and hydrodynamic groups will be combined on a 2D surface maps. The size of potential exploration areas may be extended toward the periphery of hydrodynamic groups with optimum PVT properties. In case of having neighboring hydrodynamic groups with distinct PVT properties, local structural features represent the spatial border between newly targeted and non-targeted area. Faults between hydrodynamic groups with promising PVT characteristic are considered to be of conductive nature, therefore the area between both hydrodynamic groups will present a future prospective target for exploration.

Stratigraphic and structural features may ambiguously be responsible for either the connection or for seal conditions between reservoir blocks or fields. Spatial strategies for the extension of proven exploration areas may be optimized by knowing the exact position of faults and their hydraulic functionality.

Figure 11:
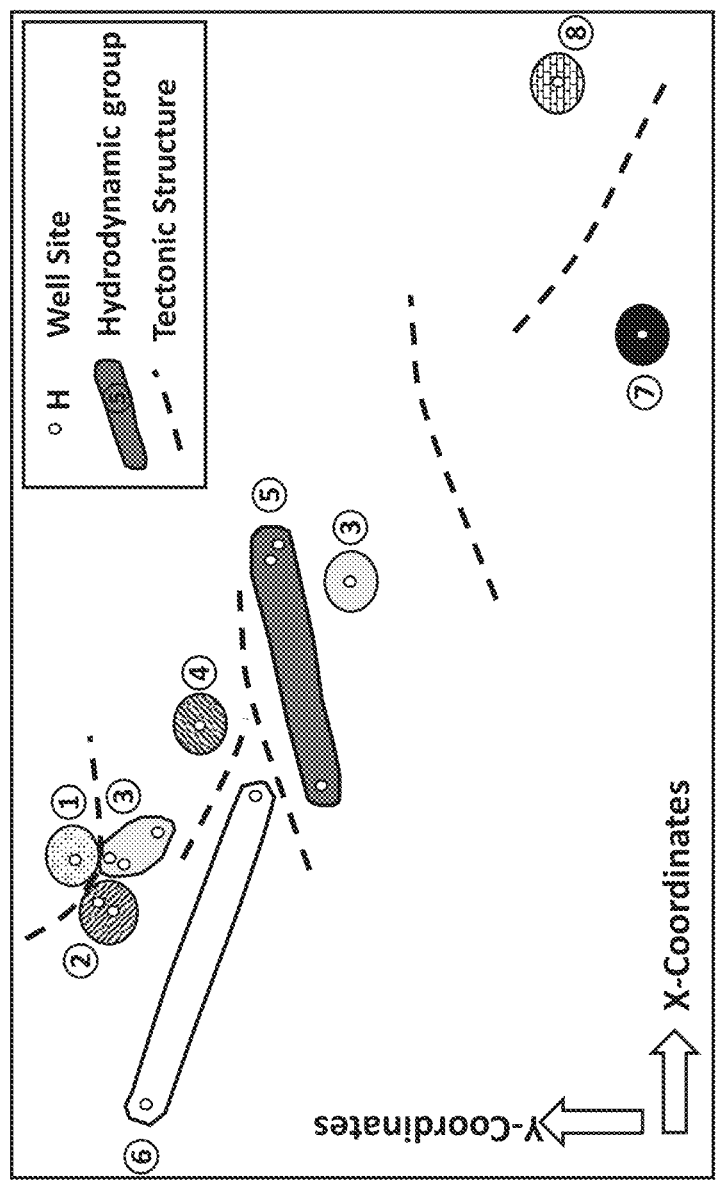
FIG. 11 shows a case study map with a combination of geochemical information hydrodynamic groups with the seismic-derived location of fault structures.

FIG. 11 shows major fault structures, from seismic interpretation, integrated to the regional map with the hydrodynamic groups (dashed lines).

With that methodology, the dimension of a proven exploration area may be extended toward a defined direction. The size of hydrodynamic groups with elevated exploration potential may be extended toward tectonic structures, which are functioning as seal toward low potential zones.

Figure 12:
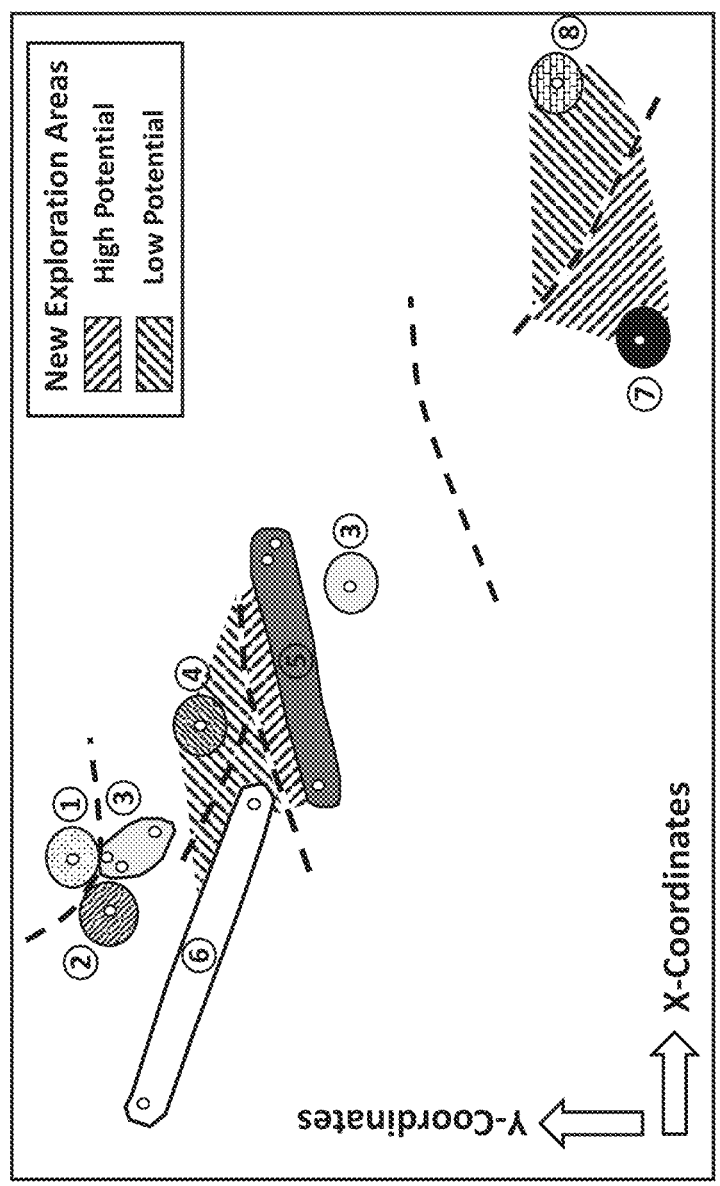
FIG. 12 shows an assessment of new exploration areas with limited and elevated (red pattern zone) potential for field expansion, based on the combined evaluation of hydrodynamic groups, structural information and well testing data.

FIG. 12 shows an example of the exploration area of hydrodynamic group 5 enlarged to the north (high potential dashed zone) with a WSW-ENE trending fault, which seals the potential area of hydrodynamic group 5 toward the surrounding areas of the hydrodynamic groups 4 and 6. As the exploration wells from hydrodynamic groups 4 and 6 showed limited hydrocarbon show-up during testing, the area between both hydrodynamic groups should be avoided for further exploration (low potential dotted zone).

Figure 13:
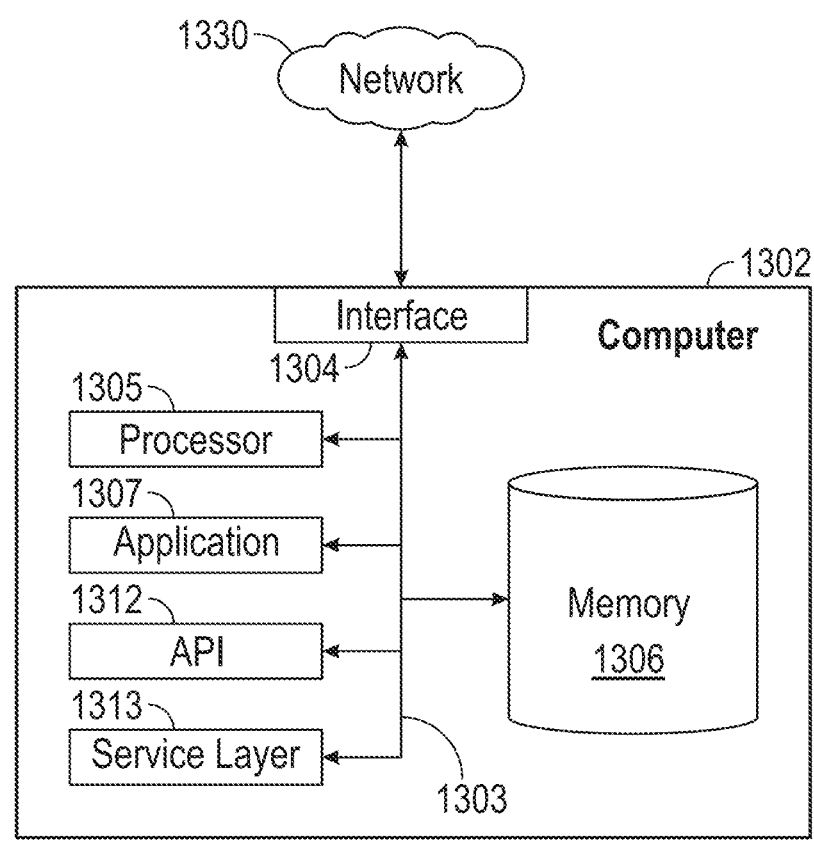
FIG. 13 illustrates a computer system, according to one or more embodiments.

FIG. 13 is a block diagram of a computer system 1302 used to provide computational functionalities associated with the method to assess reservoir continuity between single wells in an oilfield formation within a region with several petroleum reservoirs.

The illustrated computer system 1302 is intended to encompass any computing device such as a high-performance computing (HPC) device, a server, desktop computer, laptop/notebook computer, wireless data port, smart phone, personal data assistant (PDA), tablet computing device, one or more processors within these devices, or any other suitable processing device, including both physical or virtual instances (or both) of the computing device. Additionally, the computer system 1302 includes a computer that includes an input device, such as a keypad, keyboard, touch screen, or other device that can accept user information, and an output device that conveys information associated with the operation of the computer system 1302, including digital data, visual, or audio information (or a combination of information), or a GUI.

The computer system 1302 serves in a role as a client, network component, a server, a database or other persistency, or any other component (or a combination of roles) of a computer system for performing the subject matter described in the instant disclosure. The illustrated computer system 1302 is communicably coupled with a network 1330 or cloud. In some implementations, one or more components of the computer system 1302 are configured to operate within environments, including cloud-computing-based, local, global, or other environment (or a combination of environments).

At a high level, the computer system 1302 is an electronic computing device operable to receive, transmit, process, store, or manage data and information associated with the described subject matter. According to some implementations, the computer system 1302 also includes or is communicably coupled with an application server, e-mail server, web server, caching server, streaming data server, business intelligence (BI) server, or other server (or a combination of servers).

The computer system 1302 receives the dataset of the geochemical compositions of the water samples over a network 1330 or cloud from a client application (for example, executing on another computer system 1302 and responding to the received requests by processing the said requests in an appropriate software application. In addition, requests may also be sent to the computer system 1302 from internal users (for example, from a command console or by other appropriate access method), external or third-parties, other automated applications, as well as any other appropriate entities, individuals, systems, or computers.

Each of the components of the computer system 1302 communicates using a system bus 1303. In some implementations, any, or all of the components of the computer system 1302, both hardware or software (or a combination of hardware and software), may interface with each other or the interface 1304 (or a combination of both) over the system bus 1303 using an application programming interface (API) 1312 or a service layer 1313 (or a combination of the API 1312 and service layer 1313. The API 1312 includes specifications for routines, data structures, and object classes. The API 1312 is either computer-language independent or dependent and refer to a complete interface, a single function, or even a set of APIs. The service layer 1313 provides software services to the computer system 1302 or other components (whether or not illustrated) that are communicably coupled to the computer system 1302. The functionality of the computer system 1302 is accessible for all service consumers using this service layer. Software services, such as those provided by the service layer 1313, provide reusable, defined business functionalities through a defined interface. For example, the interface is software written in JAVA, C++, or other suitable language providing data in extensible markup language (XML) format or other suitable format. While illustrated as an integrated component of the computer system 1302, alternative implementations may illustrate the API 1312 or the service layer 1313 as stand-alone components in relation to other components of the computer system 1302 or other components (whether or not illustrated) that are communicably coupled to the computer system 1302. Moreover, any or all parts of the API 1312 or the service layer 1313 are implemented as child or sub-modules of another software module, enterprise application, or hardware module without departing from the scope of this disclosure.

The computer system 1302 includes an interface 1304. Although illustrated as a single interface 1304 in FIG. 13, two or more interfaces 1304 are used according to particular needs, desires, or particular implementations of the computer system 1302. The interface 1304 is used by the computer system 1302 for communicating with other systems in a distributed environment that are connected to the network 1330. Generally, the interface 1304 includes logic encoded in software or hardware (or a combination of software and hardware) and operable to communicate with the network 1330 or cloud. More specifically, the interface 1304 includes software supporting one or more communication protocols associated with communications such that the network 1330 or interface's hardware is operable to communicate physical signals within and outside of the illustrated computer system 1302.

The computer system 1302 includes at least one computer processor 1305. Although illustrated as a single computer processor 1305 in FIG. 13, two or more processors are used according to particular needs, desires, or particular implementations of the computer system 1302. Generally, the computer processor 1305 executes instructions according to the trained model and manipulates the dataset of the geochemical compositions of the water samples to perform the operations of the computer system 1302 and any algorithms, methods, functions, processes, flows, and procedures as described in the instant disclosure to output the CDP, that indicates the sand production in the formation.

The computer system 1302 also includes a memory 1306 that holds the dataset geochemical compositions of the water samples for the computer system 1302 or other components (or a combination of both) that is connected to the network 1330. For example, the memory 1306 is a database storing the dataset of the geochemical compositions of the water samples consistent with this disclosure. Although illustrated as a single memory 1306 in FIG. 13, two or more memories are used according to particular needs, desires, or particular implementations of the computer system 1302 and the described functionality. While memory 1306 is illustrated as an integral component of the computer system 1302, in alternative implementations, memory 1306 is external to the computer system 1302.

The application 1307 is an algorithmic software engine providing functionality according to particular needs, desires, or particular implementations of the computer system 1302, particularly with respect to functionality described in this disclosure. For example, application 1307 serves as one or more components, modules, applications, etc. Further, although illustrated as a single application 1307, the application 1307 is implemented as multiple applications 1307 on the computer system 1302. In addition, although illustrated as integral to the computer system 1302, in alternative implementations, the application 1307 is external to the computer system 1302.

There are any number of computers 1302 associated with, or external to, a computer system containing computer system 1302, each computer system 1302 communicating over network 1330. Further, the term "client," "user," and other appropriate terminology are used interchangeably as appropriate without departing from the scope of this disclosure. Moreover, this disclosure contemplates that many users may use one computer system 1302, or that one user may use multiple computers 1302.

The resulting information of potentially communicated reservoir sections may be utilized to reduce drilling risk by an enhanced prediction of optimum drilling sites.

Although only a few example embodiments have been described in detail above, those skilled in the art will readily appreciate that many modifications are possible in the example embodiments without materially departing from this invention. Accordingly, all such modifications are intended to be included within the scope of this disclosure as defined in the following claims.

What is claimed:

1. A method comprising:
   collecting a plurality of water samples from a plurality of wells in a reservoir region,
   obtaining, using a geochemical analysis with the plurality of water samples, a geochemical dataset describing a plurality of geochemical compositions of the plurality of wells,
   determining, by a computer processor, a plurality of principal components based on the plurality of geochemical compositions and a principal component analysis,
   wherein the plurality of principal components represent at least some of the geochemical dataset including a plurality of geochemical ratios comprising a calcium-to-magnesium ratio (Ca/Mg), a strontium-to-calcium ratio (Sr/Ca), and a sodium-to-chloride ratio (Na/Cl), representing the geochemical dataset using the plurality of principal components to obtain a reduced geochemical dataset,
   clustering, by the computer processor and using a k-means clustering algorithm, the reduced geochemical dataset to obtain a plurality of clusters,
   identifying, by the computer processor, a plurality of hydrodynamic groups within the reservoir region from the plurality of clusters,
   wherein the plurality of wells are assigned to a respective hydrodynamic group among the plurality of hydrodynamic groups based on the plurality of principal components,
   determining, by the computer processor, a plurality of hydrocarbon production potentials for the plurality of hydrodynamic groups using the plurality of clusters and a plurality of tectonic structures in the reservoir region,
   determining, by the computer processor, a location of an exploratory well within the reservoir region based on at least one hydrocarbon production potential among the plurality of hydrocarbon production potentials, and
   performing a drilling operation at the location of the exploratory well.

2. The method of claim 1, further comprising:
   coupling the plurality of hydrodynamic groups with pressure, volume, and temperature (PVT) testing data of the plurality of wells, wherein positively tested single wells in a hydrodynamic group among the plurality of hydrodynamic groups are considered to be hydraulically communicated, and negative PVT single wells in the plurality of hydrodynamic groups are considered to be hydraulically compartmentalized.

3. The method of claim 1, further comprising:
   coupling the plurality of hydrodynamic groups with a plurality of structural features of an oil-field formation, wherein two hydrodynamic groups among the plurality of hydrodynamic groups without a structural feature between them are considered to be hydraulically communicated, and a portion of the plurality of hydrodynamic groups with a structural feature between them are considered to be hydraulically compartmentalized.

4. The method of claim 3, wherein the plurality of structural features comprise faults, fractures, and dikes.

5. The method of claim 1, wherein the geochemical dataset comprises a pH parameter and a density parameter.

6. The method of claim 1, wherein the geochemical dataset comprises water hydrochemistry data, wherein the water hydrochemistry data describes total dissolved salinity (TDS).

7. The method of claim 1, wherein the plurality of water samples are filtered by applying filtering criteria to detect potential contamination of a water sample among the plurality of water samples and to select a representative water sample from each well among the plurality of wells.

8. The method of claim 7, wherein the filtering criteria is based on elevated concentrations of potassium to detect the potential contamination of the water sample.

9. The method of claim 1, wherein the reservoir region is a gas or an oil reservoir.

10. The method of claim 1, wherein the plurality of principal components are weighted before the plurality of principal components are clustered.

* * * * *